US009801371B2

(12) United States Patent
McGinniss et al.

(10) Patent No.: US 9,801,371 B2
(45) Date of Patent: Oct. 31, 2017

(54) SELF-ASSEMBLING POLYMER PARTICLE RELEASE SYSTEM

(75) Inventors: Vincent D. McGinniss, Columbus, OH (US); Robert S. Whitmore, Jr., Columbus, OH (US); K. David Monson, Powell, OH (US); Melissa S. Roshon, Hilliard, OH (US); Kevin B. Spahr, Worthington, OH (US); Steven M. Risser, Reynoldsburg, OH (US)

(73) Assignee: Battelle Memorial Institute, Columbus, OH (US)

( * ) Notice: Subject to any disclaimer, the term of this patent is extended or adjusted under 35 U.S.C. 154(b) by 768 days.

(21) Appl. No.: 13/884,542

(22) PCT Filed: Nov. 10, 2011

(86) PCT No.: PCT/US2011/060158

§ 371 (c)(1),
(2), (4) Date: May 9, 2013

(87) PCT Pub. No.: WO2012/118537

PCT Pub. Date: Sep. 7, 2012

(65) Prior Publication Data

US 2013/0231244 A1 Sep. 5, 2013

Related U.S. Application Data

(60) Provisional application No. 61/411,952, filed on Nov. 10, 2010.

(51) Int. Cl.
*A01N 25/28* (2006.01)
*A01N 25/10* (2006.01)
(Continued)

(52) U.S. Cl.
CPC ............. *A01N 25/28* (2013.01); *A01N 25/10* (2013.01); *A01N 25/34* (2013.01); *B01J 13/18* (2013.01); *B01J 13/22* (2013.01)

(58) Field of Classification Search
CPC ................................ A01N 25/26; A01N 25/28
See application file for complete search history.

(56) References Cited

U.S. PATENT DOCUMENTS 6,228,291 B1 5/2001 Lee
6,280,759 B1 8/2001 Price
(Continued)

OTHER PUBLICATIONS

Tse G et al: IIThermodynamic prediction of active ingredient loading in polymeric microparticles II, Journal of Controlled Release, Elsevi er, Amsterdam, NL, vol. 60, No. I, Jun. 28, 1999 (Jun. 28, 1999) , pp. 77-100, XP004170493, ISSN: 0168-3659, DOI: 10.1016/S0168-3659(99)00056-5.
(Continued)

*Primary Examiner* — Michael B Pallay
(74) *Attorney, Agent, or Firm* — Frank Rosenberg; C. Michael Gegenheimer

(57) ABSTRACT

Self-assembly is defined as the ability of an active ingredient (AI), when mixed with a polymer or polymers (solid or liquid state), to form either a complex or a strong attraction with the polymer/polymers, which influences the controlled release of the total system. This AI-polymer interaction or strong attraction can form in the solid state or in solution. The AI-polymer interaction also can form when applied to a filter paper, soil, seeds, or plant vegetation substrates, where the AI and polymer self-assembles into an AI-polymer-substrate matrix or complex that influences how the AI releases from the complex or matrix in a controlled manner.

11 Claims, 4 Drawing Sheets

(51) Int. Cl.

| | |
|---|---|
| ***A01N 25/34*** | (2006.01) |
| ***B01J 13/18*** | (2006.01) |
| ***B01J 13/22*** | (2006.01) |

(56) References Cited

U.S. PATENT DOCUMENTS

| | | | | |
|---|---|---|---|---|
| 6,696,089 | B2 | 2/2004 | Kabanov | |
| 6,878,446 | B2 | 4/2005 | Innako | |
| 8,084,397 | B2 | 12/2011 | Li | |
| 8,173,764 | B2 | 5/2012 | Diwan | |
| 2010/0119679 | A1* | 5/2010 | Dihora | B01J 13/16 426/534 |

OTHER PUBLICATIONS

Bromberg et al: “Polymeric micelles in oral chemotherapy”, Journal of Controlled Release, Elsevier, Amsterdam, NL, vol. 128, No. 2, Jun. 4, 2008 (Jun. 4, 2008), pp. 99-112, XP022667766, ISSN: 0168-3659, DOI: 10.1016/J.JCONREL.2008.01.018.

Gaucher G et al: “Polymeric micelles for oral drug delivery”, European Journal of Pharmaceutics and Biopharmaceutics, Elsevier Science Publishers B.V., Amsterdam, NL, vol. 76, No. 2, Oct. 1, 2010 (Oct. 1, 2010), pp. 147-158 XP027369210, I SSN: 0939-6411.

Amalina BTE Ebrahim Attia et al: “Mixed micelles self-assembled from block copolymers for drug delivery”, Current Opinion in Colloid and Interface Science, London, GB, vol. 16, No. 3, Oct. 28, 2010 (Oct. 28, 2010), pp. 182-194, XP028211425, ISSN: 1359-0294, DOI: 10.1016/J.COCIS.2010.10.003.

* cited by examiner

FIG. 1
PRIOR ART
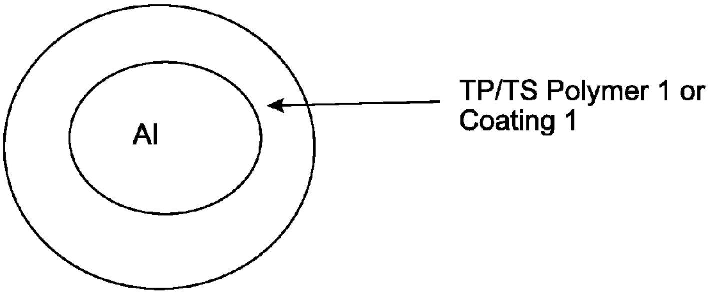
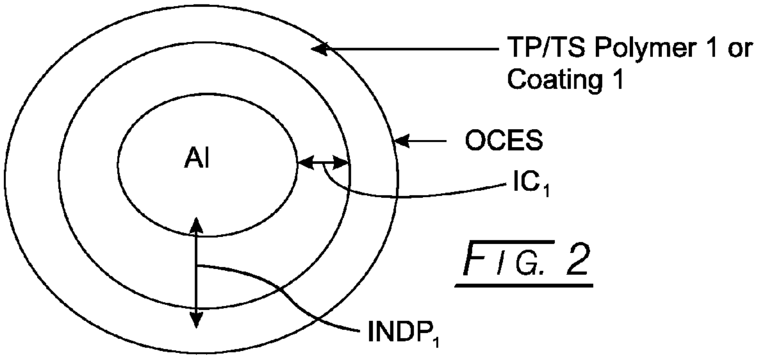
FIG. 2
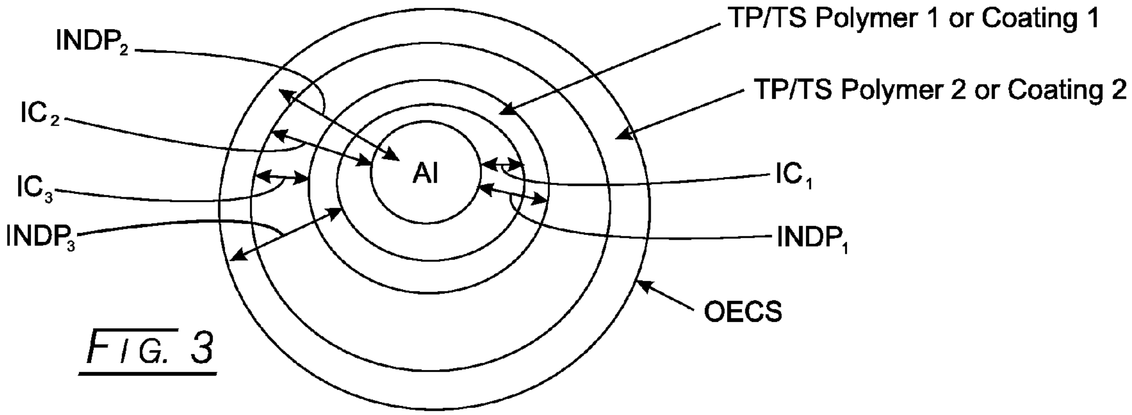
FIG. 3
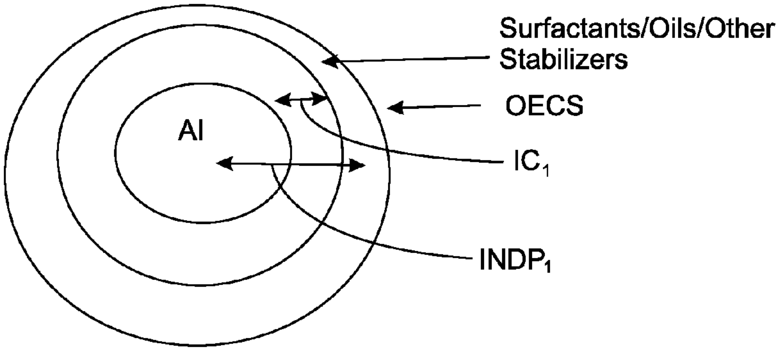
FIG. 4

FIG. 8
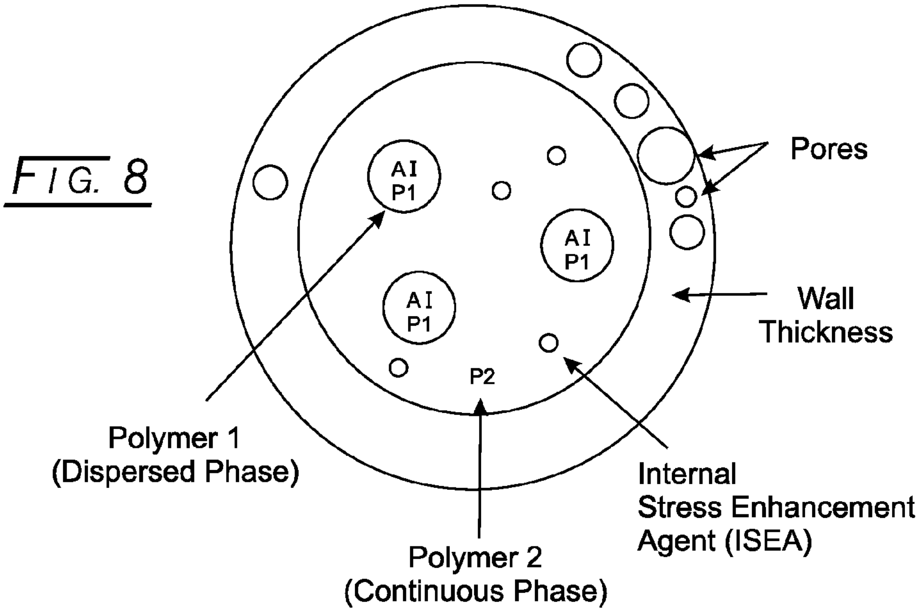
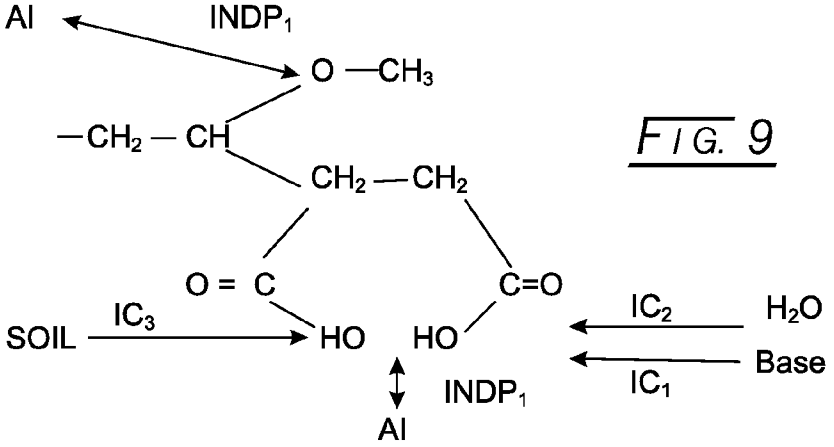
FIG. 9
FIG. 10
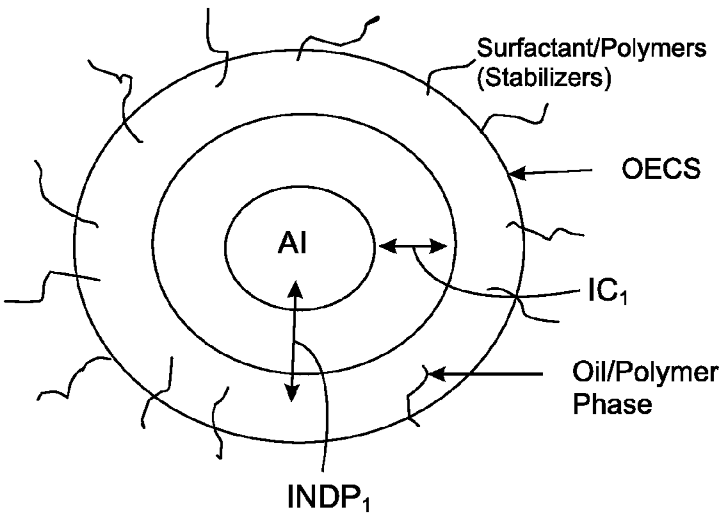

FIG. 11
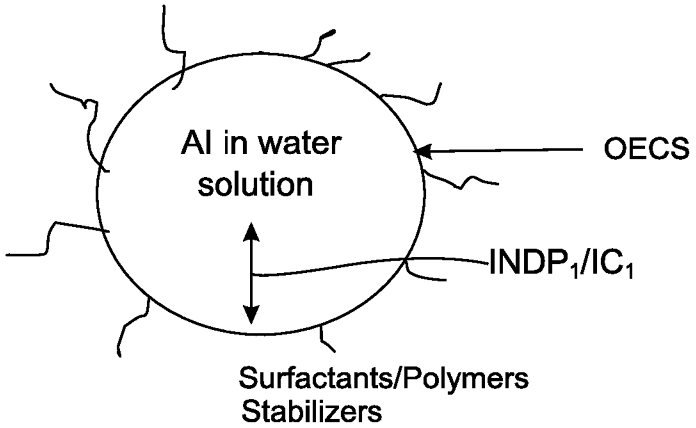
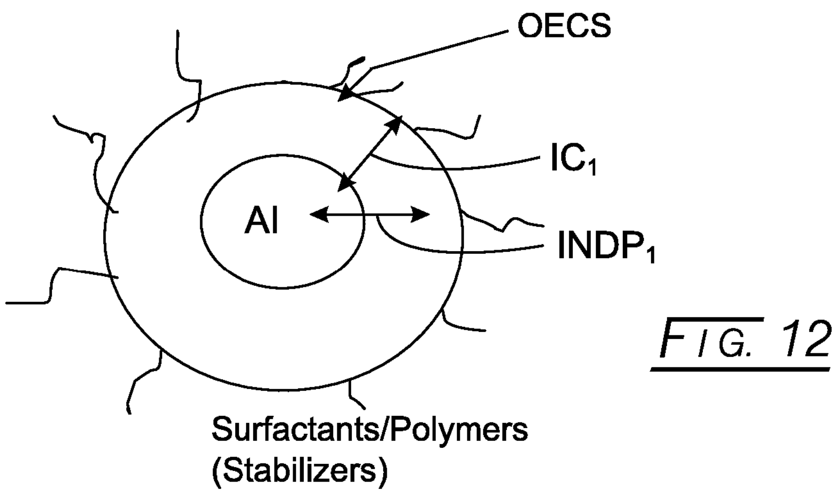
FIG. 12
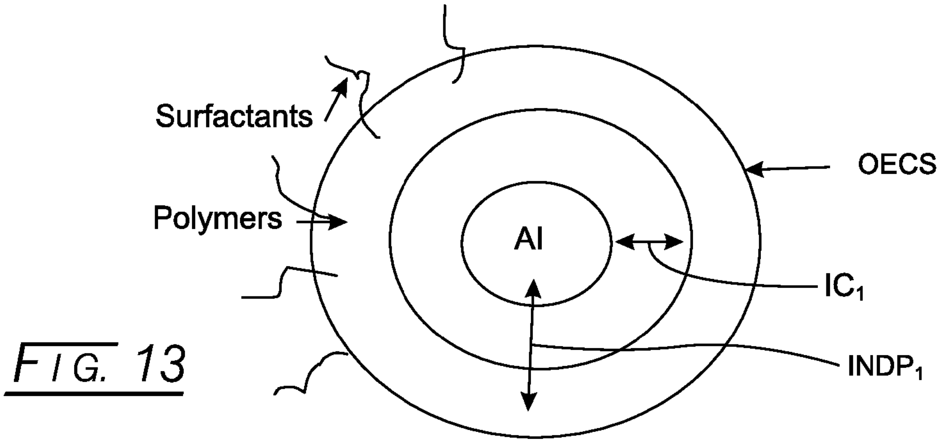
FIG. 13

SELF-ASSEMBLING POLYMER PARTICLE RELEASE SYSTEM

CROSS-REFERENCE TO RELATED APPLICATIONS

This application claims benefit of confirmed international application PCT/US2011/060148, filed Nov. 10, 2011, which claims benefit of provisional Application No. 61/411,952, filed Nov. 10, 2010, the disclosures of which are hereby incorporated herein by reference.

STATEMENT REGARDING FEDERALLY SPONSORED RESEARCH

Not applicable.

BACKGROUND

It is well known in the prior art that solid, liquid, or gaseous active ingredients can be confined into a liquid or solid core structure and used as a controlled-release product. It also is known that this basic core structure can then be further protected from the environment by a solid or liquid shell or outer coating system to produce a more complicated controlled-release product. There are a number of methods (in situ polymerization, coacervation, spray drying, interfacial polymerization) by which one can create nano to micron size or larger capsules that protect an active ingredient (AI) from its surroundings. A description of the prior art associated with the preparation of microcapsules and nanocapsules is contained in the following references.

1. Microcapsule processing and technology, Asaji Kondo (edited by J. Wade Van Valkenburg), Marcel Dekker, Inc., New York, 1979.
2. H. M. Goertz (1993) in Kirk-Othmer Encyclopedia of Chemical Technology, Vol. 7: Controlled Release Technology, Agricultural, pp 551-572.
3. Controlled-release delivery system for pesticides, H. B. Scher, editor, M. Dekker, 1999.
4. ACS symposium series; 33, Controlled release polymeric formulations, D. R. Paul and F. W. Harris, editors, 1976.
5. ACS symposium, Controlled-Release Pesticides, 1977.

PRIOR ART

U.S. Pat. No. 5,883,046 produces microcapsules of AI's by making an aqueous solution of water-soluble polymers and adding a nonaqueous phase that consists of a styrene/polyester liquid resin that contains an AI and peroxide. This oil-in-water suspension is mixed under high shear, heated to initiate the polymerization reaction, which results in microcapsules that contain the AI. The polymers disclosed in this disclosure can only be used with AI's that are nonreactive with the free radicals generated during the initiation, propagation, and termination processes associated with forming the crosslinked styrene-unsaturated polyester resin structures. The solubility parameters associated with the vinyl monomer-unsaturated polyester of the patent are limited and have an internal compatibility with only a limited class of AI compounds. The controlled-release properties of these microcapsules are also only controlled by the capsule wall thickness and degree of crosslinking of the unsaturated polyester resin; no additional controlled-release enhancements are used or suggested in the disclosure.

U.S. Pat. No. 4,534,783 encapsulates water-soluble herbicides (aqueous phase) with an oil or organic liquid and an oil-soluble alkylated polyvinylpyrrolidone emulsifier (first shell) and protective polymers, polyamide, polysulfonimide polyester, polycarbonate, or polyurethane as a second protective shell. These polymer structures are constructed by using reactive chemistries (amine or di- or polyacid chlorides and isocyanates) that can react with a number of AI's in use today. These capsules are claimed to be stable, but they do not contain, for example, a diffusion-control agent or a capsule-fracture agent that is stable in the emulsion under storage and before application but becomes active the capsules come in contact with the soil or plant surfaces. The polymer systems of this disclosure are also designed only for water-sensitive AI's. The polymers used in this disclosure are water sensitive (Modern Plastics & Encyclopedia, 1991, McGraw Hall), but there is no indication of how much of the AI is released out of the capsules during storage or after application.

U.S. Pat. No. 4,557,755 is only operable for AI's with low solubility in water (1 g/100 ml) and are encapsulated with a water-soluble cationic urea resin and prepolymers of formaldehyde, urea, melamine, and thiourea. A melamine-formaldehyde prepolymer is formed in an aqueous environment and then mixed with an aqueous urea-formaldehyde polymer; then both systems are added to an aqueous solution of a water-soluble amine salt (cationic) urea resin to form the precapsule medium. The AI is added to the precapsule medium, emulsified, and acidified to microencapsulate the AI. The major deficiency with these encapsulated products is that the only way to control the release of the AI is by changing the wall thickness of the capsule. There are no interface control agents or modifiers disclosed in this patent for controlling the release of the AI.

U.S. Pat. No. 4,344,857 uses aqueous solutions of polyhydroxy polymer starch-xanthate that can be coagulated with acids to form suspensions in the presence of AI's, which are claimed to be encapsulated then by the process. This disclosure also disclosed the use of hydrogen peroxide to produce an encapsulated AI product as well. If hydrogen peroxide comes in contact with a number of different AI structures, there is a chemical reaction that alters the chemistry of the AI. The capsules or encapsulated products of this disclosure have no size descriptions and do not have any way of controlling the release rate of an AI other than wall thickness. The polymers of these capsules are water sensitive and could not be used in a water solution/suspension application where the storage of the water/encapsulated product liquid system is greater than a one-day time period.

U.S. Pat. No. 5,599,583 used molten water-soluble polymers as the binder for AI's in a water-free encapsulation process. This process is sensitive to AI's that are water insoluble and thus, limits their use for AI structures that are more water-soluble. The long-term stability of these water-soluble polymers in an aqueous application delivery system is also expected to be very limited.

BRIEF SUMMARY

The current disclosure is a method for constructing a self-assembling polymeric particle bearing an active ingredient ("AI"). The first step is determining the solubility parameter for an AI, where the AI has a user defined characteristic not evidenced by the AI for a user defined application, such as, for example, as being too slow, too fast, too penetrating, or insufficiently penetrating. The next step is matching the AI solubility parameter with the solubility parameter of a first polymer for forming an AI/first polymer stable blend. The next step is determining a second polymeric interface control agent that assists the AI in the AI/first polymer blend to evince the user defined characteristic for the user defined application, and blending the second polymeric interface control agent with the AI/first polymer blend to form a second blend. If the second blend is not stable in water, a water-stabilizing additive is added to the second blend. The final step is making a water stable blend of the second blend and the water-stabilizing additive, if any. The thus-formed water stable, second blend forms into a self-assembled polymeric particle upon deposition of the second blend upon a surface where the self-assembling polymeric particle has a core of the AI with the first polymer, the second polymeric interface control agent, and the water-stabilizing additive, if any, enveloping the AI.

Also disclosed is the self-assembling polymeric particle bearing an active ingredient ("AI"), wherein an AI has a user-defined characteristic not evidenced by the AI for a user-defined application. The self-assembling polymeric particle also has a first polymer having a matched solubility parameter with the AI for forming an AI/first polymer stable blend. The self-assembling polymeric particle also has a second polymeric interface control agent that assists the AI in the AI/first polymer blend to evince the user defined characteristic for the user-defined application, where the second polymeric interface control agent was blended with the AI/first polymer blend to form a second blend. An optional water-stabilizing additive can be incorporated into the second blend if the second blend is not stable in water. The second blend dispersed in water forms a self-assembled polymeric particle upon deposition of the aqueous second blend upon a surface, where the self-assembling polymeric particle has a core of the AI with the first polymer, the second polymeric interface control agent, and the water-stabilizing additive, if any, enveloping the AI.

BRIEF DESCRIPTION OF THE DRAWINGS

FIG. 1 shows a prior art configuration in which active ingredients (AI) is surrounded or encapsulated with a thermoplastic (TP) or thermosetting (TS) polymer.

FIG. 2 illustrates an encapsulation model in which the interface control region ($IC_1$) between the AI and the first outer polymer 1 and the association between the AI and the outer polymer 1.

FIG. 3 illustrates a core/shell model with IC and interaction design parameters (INDPs).

FIG. 4 illustrates a core/shell emulsion model for AI, $IC_1$, surfactants/oils/other stabilizers, $INDP_1$, and outside environmental control surface (OECS).

FIG. 8 illustrates the introduction of stress enhancement agents.

FIG. 9 illustrates the interaction of maleic acid with the system.

FIG. 10 illustrates a core/shell emulsion model for AI, $IC_1$, an oil/polymer phase, stabilizers, $INDP_1$, and outside environmental control surface (OECS).

FIG. 11 illustrates that $IC_1$ and $INDP_1$ influence the way the AI is transported through soil or plant surfaces.

FIG. 12 illustrates a model in which $INDP_1$ materials keep the AI suspended in water while $IC_1$ controls the stability and release capabilities of the system.

FIG. 13 illustrates a model in which $INDP_1$ materials maintain the particle sizes.

DETAILED DESCRIPTION

Figure 5:
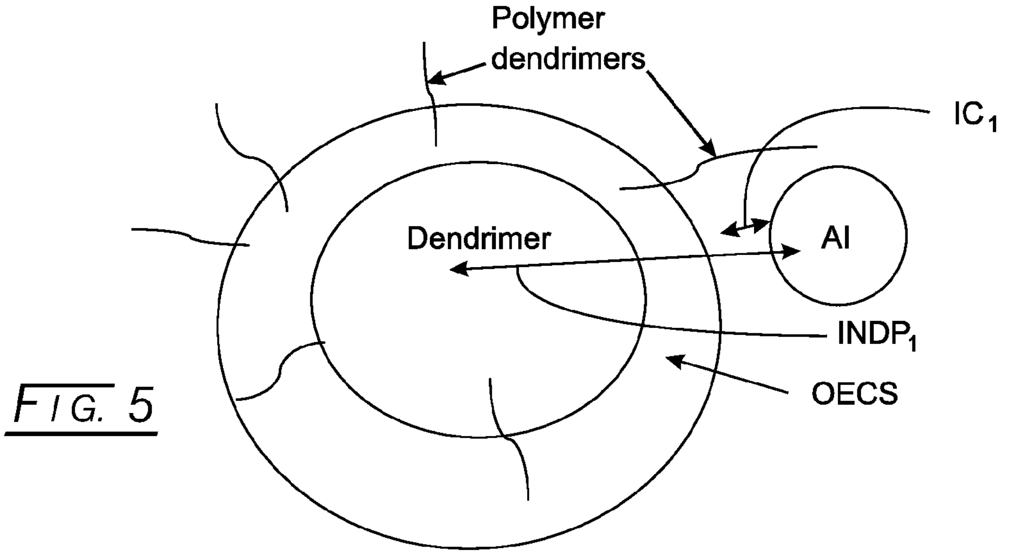
FIG. 5 a dendrimer model AI, $IC_1$, polymer densrimers, $INDP_1$, and OECS.
Figure 6:
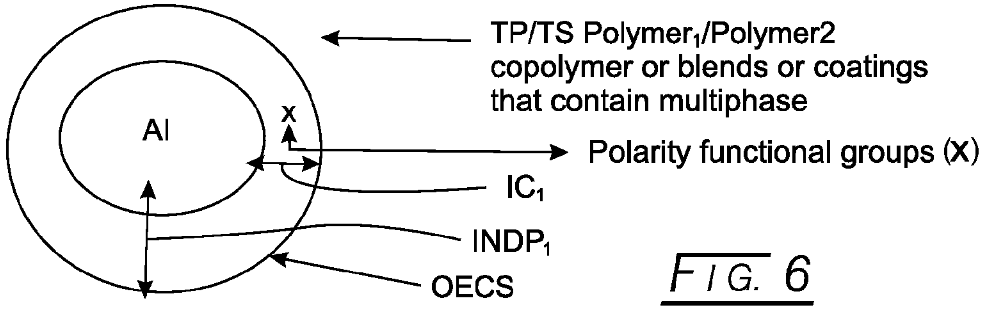
FIG. 6 illustrates an encapsulation model in which the interface control region ($IC_1$) is modified by polarity functional groups.

Before proceeding further, the following definitions and abbreviations are given.

| Abbreviation | Meaning |
|---|---|
| AI | Active ingredient |
| TS | Thermosetting |
| TP | Thermoplastic |
| OECS | Outside environment control surface |
| IC | Interface or diffusion control region of the capsule |
| INDP | Interaction design parameter (controls AI-Polymer n or $Polymer_1$-$Polymer_n$ Interactions) |
| Hansen Solubility Parameters | δT = Total solubility parameter<br>δp = polar<br>δh = hydrogen bonding<br>δd = dispersion |
| $E_o$ | Outside environment (water) that diffuses into the surface of Polymer 1 |
| $D_n$ | Diffusion of water into the surface of polymer n |
| x | Functional groups that control $IC_1$ and OCES |
| ISEA | Induced Stress Enhancement Agents |
| Tg | Glass transition temperature |
| Self assembly | Ability of an AI, when mixed with a polymer or polymers (solid or liquid state), to form either a complex or a strong attraction with the polymer/polymers, which influences the controlled release of the total system |
| S | Soil |
| IF | Polymer AI Interaction Factors |
| χ | McGinniss predictive value from McGinniss equation. The χ factor is based upon the McGinniss predictive relationship as defined in *Organic Coatings and Plastics Chemistry*, Vols. 39 and 46, pp 529-534, and 214-223, respectively, (1978 and 1982, respectively). The McGinniss predictive relationship defines the χ factor as the weight fraction of heteroatoms contained in the monomer or in the monomer repeat unit of an oligomer or polymer. See also U.S. Pat. No. 4,566,906. |

A majority of the prior art information on controlled release of active ingredients (AI) can be described by the diagram in FIG. 1, where the AI is surrounded or encapsulated with a thermoplastic (TP) or thermosetting (TS) polymer or coating.

In the present disclosure, we propose a different type of AI encapsulation model that selects and designs polymers and other materials for enhanced control of AI release capabilities not envisioned in the prior art. The AI encapsulation model of this disclosure is shown in FIG. 2 and indicates that the interface between the AI and the first outer Polymer 1 or coating 1 [thermoplastic (TP)/thermosetting (TS)] [interface or diffusion control region ($IC_1$)] and the association between the AI and the outer Polymer 1 or coating 1 (TP/TS) [interaction design parameter ($INDP_1$)] is critical for determining how the AI release process is controlled. Another feature of this disclosure is defined as the outside environment control surface (OECS).

In the prior art, however, there is no mention of how to design the interface or diffusion control region of the capsule ($IC_1$), which is defined in this disclosure as the region between the AI and the first (1) outer shell (TP/TS polymer, or coating). Also related to the prior art, there also is not a clear description on how to control the interaction of the AI with the bulk of the first (1) encapsulating shell materials. In this disclosure, the interaction design parameter ($INDP_1$) is disclosed and defined for such control (that is lacking in the prior art). The OECS helps control the overall stability of the AI system in storage and assists in controlling the interaction of the AI system with the outside environment when applied to soil or plant surfaces. The OECS can be a surfactant, a modified/functional polymer, or even an inorganic or organic filler. The OECS can be the same as the $INDP_1$ or it can be a different material.

Even in prior art core shell encapsulated products, these critical design features are not addressed, which limits the ability of their structures to reach their full potential for a controlled release of an active ingredient (AI).

A core/shell IC/INDP model for this disclosure is shown in FIG. 3 for formulations having multiple polymer coatings for the AI. Similar models of this disclosure can be depicted for emulsion (oil-in-water or water-in-oil or powder dispersions and dendrimer AI controlled-release delivery systems and are illustrated in FIGS. 4 and 5.

Figure 7:
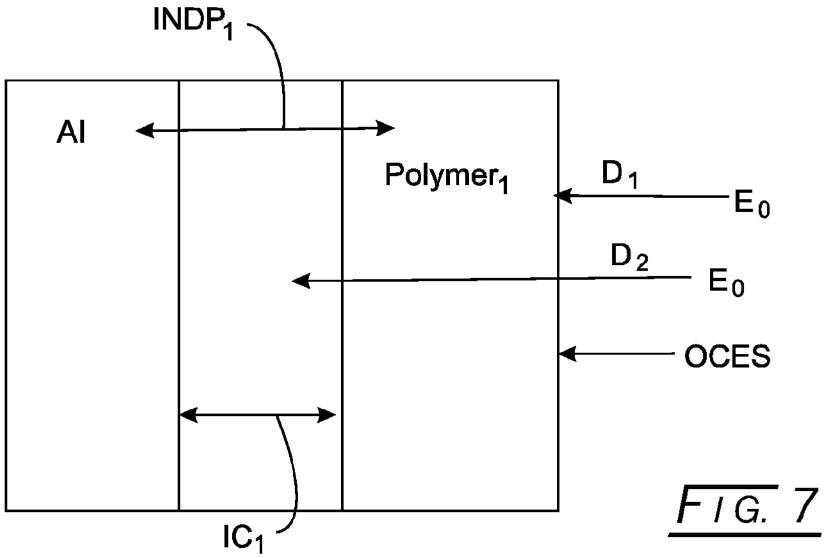
FIG. 7 illustrates another way to describe the model of the interaction between AI, $IC_1$, $polymer_1$, $INDP_1$, and OECS.

Thus the $IC_1$ interface control region in the present disclosure can be changed by putting small amounts of materials that contain functional groups (e.g., alcohols, acids, amines, hydrophobic, hydrophilics, nonionics) between the AI and the first polymer (TP/TS $polymer_1$) in contact with the AI. The materials containing functional groups that can be used as $IC_1$ modifiers can be, for example, polymers, surfactants, small molecules, plasticizers that have solubility parameters the same or different than the AI, or first polymer strongly associated with the AI through the interaction design parameter constraints. One of the critical requirements of the interface control ($IC_1$) agent for polymers is that the total solubility parameter (δT) or any of the δd, δh, and δp parameters should be at least 1 to 2 units different than the interaction design parameter ($INDP_1$) for the AI-$polymer_1$ system. FIG. 7 is another way to describe the concepts of this disclosure.

The OECS may be the same or different than the $INDP_1$ material. The OECS material could be in the outside polymer or may be external polarity (nonpolar/polar) functional groups on the outside of the polymer surface.

In this model, the $INDP_1$ is the interaction design parameter for the AI-$polymer_1$ association. $IC_1$ is the interface control region between the AI and Polymer 1. $E_o$ is the outside environment (water) that diffuses into the surface of Polymer 1 ($D_1$) and then penetrates all the way through ($D_2$) $polymer_2$ to the $IC_1$ region between the AI and Polymer 1. The interface control region and interface control or diffusion agents/functional groups influence the transport of the AI out of the capsule and the diffusion of water into the capsule (interfacial phenomena mechanisms). The $INDP_1$ model is more of a bulk phenomenon and controls the solubility of the AI in or out of the polymers.

If there is a strong interaction between the AI and Polymer 1 ($INDP_1$ is large) and if the $IC_1$ region is small (not influenced by $E_o$) and if both $D_1$ and $D_2$ are small, this would create a very stable AI internal environment; however, such a formulation would exhibit poor controlled-release properties.

If there is a weak interaction or small attraction between the AI and Polymer 1 ($INDP_1$ is small) and if the $IC_1$ region is large (strongly influenced by $E_o$) and if both $D_1$ and $D_2$ are large enough, then this would create a very unstable AI internal environment with poor controlled-release properties.

Polymer 1 and the outside surface modifications on Polymer 1 or other materials such as surfactants or inorganic fillers in or on the surface of Polymer 1 also strongly influences how the total system behaves (OECS) in storage and after application to soils or plant surfaces. The following material interactions describe a general picture of how the material interfaces are controlled in this disclosure.

1. AI-$P_1$ where $INDP_1$ is strong [close (1 to 2 units) alignment/overlap of AI and $P_1$ solubility parameters]
2. AI-$P_1$ where $INDP_1$ is weak [(some (2 to 3 units) alignment/overlap of AI and $P_1$ solubility parameters]
3. AI-$P_1$ where $INDP_1$ is nonreactive [(greater than 4 units) alignment/overlap of AI and $P_1$ solubility parameters]
4. AI-IC—$P_1$ where $IC_1$ is strongly coupled to both the AI and $P_1$, where $ICI_1$ is strongly coupled to AI but not $P_1$ or strongly coupled to $P_1$ and not the AI
5. x-$P_1$-x where x=functional groups that control $IC_1$ and OCES
6. $IND_1$ and $IC_1$=surfactants, polymers or small molecules and inorganic fillers for facilitating or hindering the rate of transport control of the AI from the capsule, either on storage or after application to a target surface (soils, plants) and its associated environment.
7. $INDP_1$ or OECS=polymers, functional polymers, small molecules, surfactants, and inorganic fillers for facilitating or hindering the rate of transport control of the AI from the capsule, either on storage or after application to a target surface (soils, plants) and the associated environment.

The definitions of solubility parameters for solvents and polymers can be found in the CRC Handbook of Solubility Parameters, second edition, A. F. Barton, CRC Press, Boca Raton, Fla., 1991, and the Polymer Handbook, 4th edition, J. Brandrup, et al., editors, John Wiley & Sons, Inc., New York, 1999.

In this disclosure, we describe several novel combinations of materials that can be put together to create excellent controlled AI release systems that operate among a number of controlled material interfaces and systems.

In this disclosure, we specially modify the polymer to control both the AI-polymer interface and the AI-polymer interaction design parameters for maximum controlled-release efficiency. The process by which we build composite or multilayer structures is as follows:

1) Develop a model (solubility parameters, surface energy, acid/base properties, log P, hydration energies, and McGinniss Equation parameters) for each AI of interest.
2) Develop a model [solubility parameters, surface energy, acid/base properties, solution viscosity, ionic/nonionic HLB, McGinniss Equation parameter (U.S. Pat. No. 4,566,906 and references therein] for polymers, oils or dendrimers that have both strong and weak associations with the AI.
3) Select those polymers that have the greatest attraction or solubilization capacity for the AI and that are related to the interaction design parameter ($INDP_n$) of the system; polymers that have a weaker association with the AI or the other polymers in the system can act as the interface control ($IC_n$) region modifiers.
4) Apply design parameters to control the interface of the outer polymer structure with both the environment in which it is stored before delivery and the environment it sees upon application to its intended target (outside environment control surface-OECS).

An other concept described in this disclosure is the introduction of stress concentrators/capsule rupture features [Induced Stress Enhancement Agents (ISEA)] that, under the right conditions and environments, cause fractures in the walls or bulk of the capsules resulting in an enhanced transport control mechanism for the AI to be removed or rapidly diffuse out of the capsule. See FIG. 8 in this regard. These special stress enhancement agents/materials or features (pores/nano to micron size ranges) induce stress or crack formation in the capsule walls and surfaces (outside/inside); the bulk of the capsule also allows water to diffuse in faster, which increases the overall rate of decomposition of the capsule and release of the AI. These special ISEA materials can be activated by changes in pH, thermal shock, or changes in temperature and mechanical or other physical mechanistic processes. Changes in crosslink density, water swelling, and multiple Tg domains can also influence the generation of stress concentrators and microvoids or pores in the capsule structure. FIG. 8 shows an AI capsule with multiple polymer dispersions and internal stress enhancement agents (ISEA) and nano/micro pore structures.

Self-Assembly AI-Soil Interactions

In this disclosure, self assembly is defined as the ability of an AI, when mixed with a polymer or polymers (solid or liquid state), to form either a complex or a strong attraction with the polymer/polymers, which influences the controlled release of the total system. This AI-polymer interaction or strong attraction can form in the solid state or in solution. The AI-polymer interaction also can form when applied to a filter paper, soil, seeds, or plant vegetation substrates, where the AI and polymer self-assembles into an AI-polymer-substrate matrix or complex that influences how the AI releases from the complex or matrix in a controlled manner.

There are at least five possible combinations of AI and polymer (P) materials in solution (aqueous or nonaqueous) where all the materials are soluble, all materials are dispersible or some materials are soluble and others are dispersible that can interact with soil (S) substrates to form intermediate complex structures as shown below:

| | | | |
|---|---|---|---|
| 1. | AI + S | $k_1$ | [AI - S complex] |
| 2. | P + S | $k_2$ | [P - S complex] |
| 3. | AI - P | $k_3$ | [AI - P complex] |
| 4. | [AI - P complex] + S | $k_3k_4$ | [AI-P complex] [AI-P-S complex] |
| 5. | AI + [P-S complex]; | $k_2k_5$ | [P-S complex] [AI-P-S complex] |

In Equation 1, if $k_1$ is large, then the AI-S complex is strong and the AI will tend to stay in the soil region where it was applied and not migrate significantly from this area. If, however, $k_1$, is small, then there is not a strong attraction between the soil and the AI and thus, the AI can migrate through the soil with ease.

Similar arguments can be made for a polymer interacting with the soil (Equation 2) to form a complex, where a large or small $k_2$ value equates to the ability of the polymer to move through the soil or stay or in the region of the soil to which it was applied.

In our disclosure, we discovered that some AI-polymer combinations form a complex or unique association when applied to filter paper, dried, and subsequently washed with water, resulting in a controlled-release process for the AI (Equation 3). If the special polymer material is not present, then there is nothing to hold or associate with the AI, and it passes through the filter paper rapidly. We also observed very similar results when these AI-polymer combinations were applied to soils.

In the case of the application of an AI/polymer combination, the soil plays an important role in determining which competing complex structures are formed and thus, strongly influences the control rate of the entire system.

For example, if the AI-P complex association in solution is strong ($k_3$ is large), then when this system is applied to the soil, several possible situations can develop. In the first case (Equation 4), if both $k_3$ and $k_4$ are large, then the AI may not be easily released when rain occurs and thus, the migration of the AI-through the soil would be retarded. If, however, the AI-polymer complex is weakened by the soil ($k_3$ is small but $k_4$ is large), then the AI would have a tendency to be released from the polymer and migrate through the soil. Another situation can also occur when the $k_3$ of the AI-polymer complex is large but the $k_4$ soil interaction parameter is small; then it is possible that the AI-polymer complex as a whole migrates through the soil and slowly releases the AI in the process.

There also is the possibility that the polymer has a greater tendency to form a complex with the soil first, then is followed by a late interaction with the AI. In this case, if both $k_2$ and $k_5$ (Equation 5) are large, then the AI would tend to stay in the region where the polymer-soil complex is formed. If either $k_2$ or $k_5$ are small, then migration of the AI through the soil might be favored.

In this disclosure, we define which AI and polymer structures and parameters need to be combined in a unique manner to facilitate the controlled release of an AI when applied to a soil substrate.

This same type of argument can also be made for the AI and polymers of this disclosure and interacting with a plant, filter paper, plant surfaces or seeds, or other types of porous or nonporous surfaces.

In this disclosure, we demonstrated the AI-polymer self-assembly process on filter paper first and then verified that the same self-assembly results observed on the filter paper also applied to a soil test.

McGinniss Equations

The McGinniss Equations were first published ("Prediction of Solvent and Polymer Characteristics Through the Use of Easy to Measure Properties") by Vincent D. McGinniss in the ACS Organic Coatings and Plastics Chemistry, Volume 39, Preprints of Papers, ACS, Division of Organic Coatings & Plastics Chemistry, Miami Beach Fla., Sep. 10-15, 1978, pp 529-534.

A complementary paper ["Prediction of Solvent and Polymer Characteristics (correlation with Physical Properties and Chemical Structures")] was published in the Organic Coatings and Applied Polymer Science Proceedings, VOL 46, Preprints of Papers Presented by the Division of Organic Coatings and Plastics Chemistry, $183^{rd}$ National Meeting, Las Vegas, Nev., Mar. 25-Apr. 2, 1982, pp 214-223.

Additional publications and applications of these equations can be found in U.S. Pat. No. 4,566,906 (Anti-Fouling Paint Containing Leaching Agent Stabilizers) and U.S. Pat. No. 4,877,988 (Piezoelectric and Pyroelectric Polymers) and Polymer Vol. 36, No. 6, pp. 1127-1131, 1995 (Determination of the piezoelectric/pyroelectric response of polytrifluorovinyl acetate and other piezoelectric materials.

A wide range of chemical/physical, electrical and mechanical properties of materials can be correlated with their chemical structures by using the McGinniss equations. The McGinniss Equations are a linear or nonlinear combinations of noncarbon weight fraction of Heteroatoms ($\chi_{Heteroatoms}$) in the materials of interest and their weight fraction of $\pi$ electrons (z'), if needed to correlate aromatic/vinyl substituted materials with structures that do not contain unsaturation.

For example $CH_2{=}CHO_2CH_3$ (Vinyl acetate) has a formula weight of 86.09 and the heteroatom is oxygen and it has $2\pi$ electrons. The McGinniss Equation Parameter $\chi_O=2\times$ 16 atomic weight of Oxygen)/86.09=0.37 and z'=$2\pi$ electrons/86.09=0.023.

$CH_2{=}CHCl$ (Vinyl chloride) has a formula weight of 62.50 and $2\pi$ electrons so $\chi_{Cl}$=35.45/62.50=0.57 and z'=2/62.50=0.032

In its general form the McGinniss Equation is as follows:

Desired Response of a Material=linear function of {[an experimentally determined variable (optional)]$\pm\chi_{Heteroatoms}\pm z'$}

The Desired Response of a material can also=nonlinear function of {[an experimentally determined variable (optional)]$^n$ X or $\pm(\chi_{Heteroatoms})^n\pm(z')^n$} where n=1-3.

In this disclosure, $K_{OC}$ for the AI's of interest=function of Log P, or the water solubilities of the AI's, and the McGinniss Equation Parameters $\chi_{Heteroatoms\ O,Cl,F,N,S,P}$.

The results of the equations are determined by linear or nonlinear multiple regression analysis techniques using standard statistical analysis packages, such as, for example, NCSS97.

Active Ingredients

Exemplary active ingredients for encapsulation in this disclosure can include, for example, fungicides such as, for example, captan; any of the ethylene bisdithiocarbamate (EBDC) group of fungicides (e.g., mancozeb, maneb, niram, metiram, zineb, and ferbam); chlorothalonil; iprodione; ziram; copper salts; and sulfur.

Insecticides for encapsulation include, for example, ethion; ethyl parathion; diazinon; endosulfan; solid and liquid forms of the carbamates.

Herbicides that can be encapsulated include, for example, trifluralin; paraquat; glyphosate; alachlor and phenoxys and salts of acids like 2,4-D. A complete listing of pesticides of interest to this disclosure can be found in the pesticide index, $5^{th}$ edition, W. J. Wiswesser, editor, the Entomological Society of America, 1976.

Active ingredients, then, broadly have the function of controlling a target species. In turn, "control" means to repel, attract, kill, or exert a desired action on a target species. Target species comprehends (e.g., any living organism including, inter alia, plants, animals, fungi, bacteria, viruses, insects, fish, mollusks, and the like). AI often are called pesticides, herbicides, fertilizers, growth regulators, and the like.

General Experimental Conditions

Polymer-AI (Active Ingredient) Interaction Design Parameter and Interface Control Combinations All of the polymers in this set of experiments were combined with the AI at a 70% AI by weight to 30% polymer by weight concentrations. The dry mixture of the 70/30 AI/polymer combination was added to methylene chloride to make an 83% methylene chloride/17% mixture solution. Further, 250 µl of each solution mixture was placed on a Whatman 5.5 cm filter paper #2 (8 µm) qualitative (8161) and allowed to dry overnight. The filter paper samples were applied to a slightly wet Buchner funnel to set the paper evenly and then ten 10-ml aliquots of de-ionized (DI) water were suctioned through the filter paper. Ultraviolet light (UV) analysis for each of the 10-ml fractions was used to determine the absorption of the AI (264 nm) washed through the filter paper and recorded as absorption versus each individual 10-ml wash.

The control for these systems was evaluated by placing methylene chloride solutions of the AI alone or the polymer alone onto the filter paper, drying overnight, and washing with ten 10-ml aliquots of DI water. In all cases, the AI control came through with filter paper in fewer washings than the AI and polymer concentrations. The control polymers alone did not show any signs of UV absorption in the 264 nm region of the spectrum.

Preformed Polymer Cage (Nano to Micron or Greater Size Range)

AI Interaction Design Parameters and Interface Control Combinations

The AI was dry ground (mortar and pestle) with urea-formaldehyde flower foam as the cage material [commercial product (Foliage Fresh)] where the ratio of AI to flower foam was 70%/30% by weight. This mixture then was tumbled-coated with an organic solvent solution of a hydrophobic polymer (paraffin wax/hexane; polystyrene/toluene; silicone oil/toluene) in a round bottom flask. The solvent was removed and a dry powder of the AI/flower foam/hydrophobic polymer was obtained (62% AI)/31% flower foam/7% hydrophobic polymer). Small amounts (0.07 g) of the powder were placed on the filter paper and subsequently washed with ten 10-ml aliquots of DI water and analyzed in a similar manner as previously described.

Testing and Evaluation of AI-Polymer Combinations and Control (AI Alone) Samples Liquid samples of the AI-polymer combinations and AI control samples were applied to filter paper (Whatman #2) and dried for 24 hours at room temperature. The filter paper containing the AI-polymer combination or the AI control samples were placed in a Buchner funnel under water aspiration vacuum conditions, while ten 10-ml aliquots of water were applied to the top of the filter paper containing the AI-polymer or AI control material, which was then sucked through the filter paper and collected in the receiving flask that holds the funnel-vacuum attachment.

After each 10-ml aliquot of water was suctioned through the filter paper containing the sample, the suctioned solution then was removed and analyzed with a UV spectrometer for any AI that went through the water washing process. The ten 10-ml sequential washings were a simulation of how an AI applied to soil would remain on the soil and migrate through the soil under a rain environmental exposure condition. In all cases, the AI control (no polymer stabilization additive) passed through the filter paper in one to three 10-ml washes of water, while the AI-polymer stabilized system of this disclosure did not wash completely through the filter paper after five to ten 10-ml washing, which indicated that the stabilized AI-polymer system should have much better controlled-release characteristics than the AI-controls alone.

Dry 100% solid samples were placed on the filter paper directly and subsequently washed with ten 10-ml aliquots in a similar manner as the liquid samples that were dried after placement on the filter paper.

Various concentrations of the AI's were dissolved in water or water and a co-solvent and analyzed at 254 nm or other UV/visible regions of the spectrum in order to establish a standard calibration curve of absorbance versus AI concentration.

Example 1

Polymer-AI Interaction Design Parameter and Interface Control Combinations

In this disclosure, a solubility parameter model is constructed for the AI of interest followed by determining which polymer structures have similar solubility parameters as the AI, such that a unique environment (interaction design parameter) is created between the AI-polymer interfaces. The active ingredients chosen for the polymer-AI combinations were Imazapyr, Imazethapyr, [both referred to as IMI's or Active Ingredients (AI's)]2,4-D, Dicamba, Nicosulfuron, and Sulfentrazone.

The starting point for the model was to match the Imazapyr and Imazethapyr known solubilities in different solvents with the Hansen solubility parameters (δd=dispersion; δp=polar; δh=hydrogen bonding; δt=total solubility parameter) for these solvents.

For example, in Table 1, below, Imazapyr, and Table 2, Imazethapyr lists the solubility (g/100 ml solvent) of Imazapyr and Imazethapyr in four different solvents and their associated solubility parameters.

The solubility parameters of DMSO are equivalent to the solubility parameters of the IMI compounds.

Polymers having similar solubility parameters as DMSO should be good solvents for IMIs.

Polymer IMI Interaction Factors=IF $IF=[\delta dP-\delta dIMI)^2+(\delta pP=\delta hIMI)^2+(\delta hP-\delta hIMI)^2]^{1/2}$ where δdP, δpP, δhP, δdIMI, δhIMI are the solubility parameters for the polymers and IMI's, respectively.

Solubility of IMIs=Function of δd and δp of the polymers. PCT

TABLE 1

Imazapyr Solvent Interactions

| Solvent | Solubility | δd | δp | δh |
|---|---|---|---|---|
| Acetone | 3.39 | 15.5 | 10.4 | 7 |
| DMSO | 47.1 | 18.4 | 16.4 | 10.2 |
| Methylene Chloride | 8.72 | 18.2 | 6.3 | 6.1 |
| Methanol | 10.5 | 15.1 | 12.3 | 22.3 |
| Toluene | 0.185 | 18 | 1.4 | 2 |

Solubility = 7.426(δd) + 3.06(δp) − 141.09
$R^2 = 0.97$

TABLE 2

Imazethapyr Solvent Interactions

| Solvent | Solubility | δd | δp | δh |
|---|---|---|---|---|
| Acetone | 4.82 | 15.5 | 10.4 | 7 |
| DMSO | 42.25 | 18.4 | 16.4 | 10.2 |
| Methylene Chloride | 18.48 | 18.2 | 6.3 | 6.1 |
| Methanol | 10.5 | 15.1 | 12.3 | 22.3 |
| Toluene | 0.5 | 18 | 1.4 | 2 |

Solubility - 7.26(δd) + 2.56(δp) − 132.28
$R^2 = 0.98$

In Table 3, we selected a set of commercial polymers that had solubility parameters close to those of DMSO. In Table 4, we calculated the interactive factors between the IMI product and the polymer and the calculated DMSO polymer solubilities using the parameters and equations shown in Tables 1, 2, and 3. Polymers with higher solubility and smaller the interaction values had a greater chance of being the more compatible with the IMI products.

TABLE 3

Polymers Having Solubility Parameters Close to DMSO

| Polymers | δd | δp | δh | δt |
|---|---|---|---|---|
| CA | 18.6 | 12.73 | 11.01 | 25.08 |
| PVOAC | 20.93 | 11.27 | 9.66 | 25.66 |
| PVB | 18.6 | 4.36 | 13.03 | 23.12 |
| PAN | 18.21 | 16.6 | 6.75 | 25.27 |
| PVC | 18.72 | 10.3 | 3.07 | 21.46 |
| PSTY | 21.8 | 5.75 | 4.3 | 22.47 |
| P4OHSTY | 17.6 | 10 | 13.7 | 24.55 |
| NYLON 66 | 18.62 | 5.11 | 12.28 | 22.87 |

CA = cellulose acetate; PVOAC = polyvinyl acetate; PVB = polyvinylbutyral; PAN = polyacrylonitrile; PVC = polyvinyl chloride; PSTY = polystyrene; P4OHSTY = poly-4-hydroxystyrene.

TABLE 4

Polymer IMI Interactions and Solubilities

| Polymer-IMI | Interaction Factors (IF) | Equation Calculated Solubilities |
|---|---|---|
| CA-IMI | 3.76 | 35.9 |
| PVOAC-IMI | 5.75 | 48 |
| PVB-IMI | 12 | 10.26 |
| PVC | 9.3 | 28.5 |
| P4OHSTY | 7.2 | 20.1 |

The modeling studies indicated that two polymer materials, polyvinyl acetate (PVOAC) and cellulose acetate (CA) should theoretically have the best chance of interacting strongly with Imazapry (now designated as the AI). These combinations fit the interaction design parameters of this disclosure in that there is a maximum association of the AI with these polymers as determined by their solubility parameter compatibility values. Solid polymer samples were prepared, tested, and evaluated for their AI retention capabilities; the results are shown in Table 5.

TABLE 5

Example 1 Interaction Design Parameter ($INDP_1$) Results (Polymers + AI)

| Number of Washings and R Values | UV Absorbance at 264 μm AI Control (% Released) | Cellulose Acetate (% Released) | Polyvinyl Acetate (% Released) | (% Released) |
|---|---|---|---|---|
| 1 | 49 | 74 | 12 | 29 |
| 2 | 47 | — | 11 | 33 |
| 3 | 4 | 4 | 13 | 0 |
| 4 | 0 | 10 | 24 | 8 |
| 5 | 0 | 4 | 24 | 5 |
| 6 | 0 | 2 | 11 | 5 |
| 7 | 0 | 2 | 0 | 5 |
| 8 | 0 | 1 | 0 | 5 |
| 9 | 0 | 1 | 3 | 4 |
| 10 | 0 | 1* | 1* | 2* |
| R | 3 | 10 | 10 | 10 |

*Not all of the sample was released after 10 washings.

These results clearly show the advantage of the polymer-AI interaction design parameters control for controlled release over that of the AI alone.

A rating factor, R, can be established to clearly show the differences between the effect of ten 10-ml water washings of an unassociated or non-encapsulated AI absorbed on filter paper (control) and the AI-polymer system of this disclosure. In the results shown in Table 6, the AI control was completely depleted after 3 washings (R=3), while the cellulose acetate and polyvinyl acetate AI-samples required over 10 washings (R=10) to almost fully deplete the sample from the filter paper surface. The percent released for each system was determined from each of the individual 10-ml washing AI absorbance values ($Abs_{n=1-10}$) divided by the total absorbance values for all 10 washings ($Abs\ Total=Abs_1+Abs_2+Abs_{10}$) times 100.

The examples shown in Table 5 represent AI-polymer systems with high interaction capabilities (similar solubility parameters), which control the interaction design parameter of the disclosure.

In order to modify the interface between AI and the bulk of the encapsulation polymer, we need to either slightly change the surface of the polymer so that it contains small amounts of a functional group (acid, alcohol, hydrophobic materials) or add another additional polymer material with different solubility parameter to the system for the interface control function of the disclosure. Examples of interface control materials (IC) for modification of the AI-polyvinyl acetate samples in Table 5 are shown in Table 6 along with their IF and differences between their solubility parameters.

TABLE 7

Combinations of Interaction Design Parameters ($INDP_1$) and Interface Control ($IC_1$) polymer-AI combination

| Number of Washings and R Values | AI Control (% released) | Polyvinyl Acetate + AI ($INDP_1$) (% released) | Polyvinyl Acetate ($INDP_1$) + ($IC_1$) + AI (% released) | Polyvinyl Acetate ($INDP_1$) + ($IC_1$) + AI (% released) |
|---|---|---|---|---|
| 1 | 49 | 29 | 17 | 25 |
| 2 | 49 | 33 | 18 | 25 |
| 3 | 2 | 0 | 15 | 22 |
| 4 | 0 | 8 | 13 | 15 |
| 5 | 0 | 5 | 8 | 10 |
| 6 | 0 | 5 | 6 | 3 |
| 7 | 0 | 5 | 6 | 0 |
| 8 | 0 | 5 | 6 | 0 |
| 9 | 0 | 4 | 4 | 0 |
| 10 | 0 | 2* | 3* | 0 |
| R | 3 | 10 | 10 | 6 |

*Not all of the sample was released after 10 washings.

The results in Table 7 show the effect of the interface control polymers on the controlled release of the polyvinyl acetate ($INDP_1$)-AI system. All of the $IC_1$ polymers have solubility parameter values that differ from the pure polyvinyl acetate by 1 to 8 units or the polymer can contain a different functional group (polar, nonionic —OH group) for interface control.

In a similar manner, the solubility parameters were identified for 2,4-D, Dicamba, Nicosulfuron, and Sulfentrazone

TABLE 6

(Interface Control Polymers)

| Polymers ($IC_n$) | Solubility Parameters δd Dispersion | δp Polar | δh hydrogen Bonding | δ Total | IF | Solubility Parameter Differences [INDP1-ICn] (δd, δp, δh, δT) | | | |
|---|---|---|---|---|---|---|---|---|---|
| Polyvinyl acetate (control)(INDP1) | 20.93 | 11.27 | 9.66 | 25.66 | 0 | — | — | — | — |
| Polymer acetate-polyvinyl alcohol | 19.1 | 13.21 | 12.53 | 26.4 | 3.9 | 1.83 | 1.94 | 2.87 | 0.74 |
| Polyvinyl butyral | 18.6 | 4.36 | 13.03 | 23.12 | 8.03 | 2.33 | 6.91 | 3.37 | 2.54 |
| Polymethyl methacrylate | 21.28 | 5.75 | 4.3 | 27.47 | 7.70 | 0.35 | 5.52 | 5.36 | 1.81 |
| Polystyrene | 18.64 | 10.52 | 7.51 | 27.69 | 3.22 | 2.29 | 0.75 | 2.15 | 2.03 |
| Alcohol soluble rosin | 20 | 5.8 | 10.9 | 23.5 | 5.7 | 0.93 | 5.77 | 1.24 | 2.16 |
| Polyethylene oxide | 17.2 | 3.0 | 9.4 | 19.9 | 9 | 3.77 | 8.27 | 0.26 | 5.76 |
| Alkyd (short oil) | 18.5 | 9.21 | 4.91 | 21.24 | 5.72 | 2.43 | 2.06 | 4.75 | 4.42 |
| Alkyd (long oil) | 20.42 | 3.44 | 4.56 | 21.2 | 9.3 | 0.51 | 7.03 | 5.1 | 4.46 |
| Polystyrene-co-methyl methacrylate (40/60) | 20.39 | 5.8 | 6.15 | 22.1 | 6.53 | 0.54 | 5.46 | 3.51 | 3.58 |
| Polyvinylbutyral (80) Covinyl alcohol (17) Covinyl Acetate (3) | 19.98 | 7.62 | 13.21 | 25 | 5.18 | 0.95 | 3.65 | 3.55 | 0.66 |

Polyvinyl acetate (90% by weight) was combined with either 10% by weight of polyvinylbutyral/polyvinybutyral-covinyl alcohol-covinyl acetate or polystyrene-methylmethacrylate interface control ($IC_1$) polymers (all obtained from Aldrich Chemical Company) and each system was dissolved in methylene chloride along with the AI (IMI acid) and applied to filter paper in a similar manner as discussed previously. The results of the ten 10-ml water-washing studies are shown in Table 7.

and the polymers having the greatest interaction potential (best match of the solubility parameters with the AI's) are shown in Table 8.

TABLE 8

AI-polymer Solubility Parameters

| AI | AI/ Solvent | Solvent δ $MPA^{1/2}$ δd | δp | δh | Polymer |
|---|---|---|---|---|---|
| 2,4-D | DMSO | 18.4 | 16.4 | 10.2 | Polyvinyl acetate |
| Dicamba | Dioxane | 19 | 1.8 | 7.4 | Rosin resins |

TABLE 8-continued

| AI-polymer Solubility Parameters | | | | | |
|---|---|---|---|---|---|
| | AI/ | Solvent δ MPA$^{1/2}$ | | | |
| AI | Solvent | δd | δp | δh | Polymer |
| Nicosulfuron | Dichloro-methane | 12.3 | 2 | 0 | Butadiene polymers, petroleum hydrocarbon resins |
| Sulfentrazone | Acetone | 15.5 | 10.4 | 7 | Polyethyl methacrylate |

Examples of other types of commercially available hydrophilic or hydrophobic polymer materials that can be used in this disclosure are shown in Table 9.

TABLE 9

| Hydrophilic and Hydrophobic Polymers (Sigma Aldrich Material Science 2008-2010 Catalog, pages 260-283) |
|---|
| Polyacrylamide |
| Polyacrylamide-co-acrylic acid |
| Poly(2-acrylanido-2-methyl-1-propanesulfonic acid) |
| Polyacrylic acid and their salts |
| Poly(acrylic acid co-maleic acid) |
| Poly(acrylics acid) partial sodium salt-grafted-poly(ethylene oxide) |
| Poly(ethylene-alt-maleic anhydride) |
| Poly(methyl vinyl ether-alt-maleic acid) |
| Poly(2-hydroxyethyl methacrylate) |
| Poly(2-hydroxypropyl methacrylate) |
| Poly(methacrylic acid) and their salts |
| Poly(1-vinylpyrrolidone-co-2-dimethylamine ethyl methacrylate) |
| Cucurbit[7] uril |
| Poly(allylamine) |
| Poly(ethyl-2-oxazoline |
| Glycerol propoxylate |
| Poly(methyl vinyl ether) |
| Polystyrene sulfonated and their salts |
| Poly(vinyl sulfate) and their salts |
| Poly(vinyl sulfonic acid) |
| Poly(vinyl alcohol) |
| Poly(vinyl acetate/vinyl alcohol) |
| Poly(vinyl alcohol-co-ethylene) |
| Low alkyl ester of acrylic and methacrylic acid |
| Polyglycols and polyethylene oxides |
| Poly(butyl acrylate) |
| Poly(alkyl esters of acrylic and methacrylic acids)\ |
| Acrylonitrile polymers |
| Poly(maleic anhydride-alt-1-octadecene) |
| Poly(benzyl methacrylate) |
| Poly(cyclohexyl methacrylate) |
| Copolymers of the alkyl esters of acrylic and methacrylic adid |
| Nylon 6; Nylon 6,6,; Nylon 6,10; Nylon 6,12; Nylon 11 |

TABLE 9-continued

| Hydrophilic and Hydrophobic Polymers (Sigma Aldrich Material Science 2008-2010 Catalog, pages 260-283) |
|---|
| Polyimides |
| Polycarbonates |
| Polydienes |
| Polyester |
| Polyisoprene-graft-maleic anhydride |
| Polyurethanes |
| Polyvinyls |
| Polybutenes |
| polyolefins |

Example 2

Interaction Design Parameter ($INDP_1$) Preformed Polymer Cage (Nano to Micron or Greater Size Range)

AI Interface Control ($IC_1$) Combinations

In this example, the IMI acid or the IMI salt (isopropyl amine neutralized IMI acid) was combined with a cross-linked polymer (flower foam) and coated with a low surface energy material like a hydrophobic polymer (6% paraffin wax in hexane or silicon oil) and the results are shown in Table 10. From this study, one can clearly see the difference between the controls which start to be depleted after 4 to 6 washes, while the $INDP_1$/$IC_1$ samples continue to deliver the IMI acid after 10 washes with 10-ml aliquots DI water when analyzed in a similar manner as Example 1.

The interaction design parameter ($INDP_1$) for this example is the urea-formaldehyde crosslinked cage structures that are very water absorbing and thus interact very strongly with the water sensitive IMI acid and salt AI compounds. The interface control ($IC_1$) polymer is a hydrophobic material, such as paraffin wax, polystyrene, silicon oils, vegetable oils (soybean oil), or other hydrophobic materials (low/medium surface energy materials [siloxanes/fluorocarbons/stearic acid/hydrocarbon resins/polyvinyl methyl ether/polyolefins: 6 to 32 MJ/m$^2$, while acrylics/polystyrenes are 32 to 36 MJ/m$^2$], which coat the surface of the flower foam particles containing the AI which ultimately controls the final AI release capability of the total system. The reverse situation also can occur where the cage material is hydrophobic and the $IC_n$ is water sensitive or has high surface energy characteristics like starches/polyvinyl alcohol/polyethylene oxides: 36 to 44 MJ/m$^2$.

TABLE 10

| Example 2 Results (cage polymers + IMI acid + paraffin) | | | | | |
|---|---|---|---|---|---|
| Number of Washings | IMI Acid Control (% released) | IMI Salt Control (% released) | Cage Polymer + IMI Salt (% released) | Cage Polymer + IMI Acid + Paraffin (% released) | Cage Polymer + IMI Salt + Silicon oil (% released) |
| 1 | 41 | 43 | 30 | 3 | 10 |
| 2 | 39 | 32 | 20 | 3 | 10 |
| 3 | 14 | 13 | 20 | 5 | 10 |
| 4 | 6 | 6 | 15 | 10 | 11 |
| 5 | 0 | 6 | 10 | 15 | 11 |
| 6 | 0 | 0 | 5 | 15 | 10 |
| 7 | 0 | 0 | 0 | 13 | 10 |
| 8 | 0 | 0 | 0 | 12 | 10 |

TABLE 10-continued

| Example 2 Results (cage polymers + IMI acid + paraffin) | | | | | |
|---|---|---|---|---|---|
| Number of Washings | IMI Acid Control (% released) | IMI Salt Control (% released) | Cage Polymer + IMI Salt (% released) | Cage Polymer + IMI Acid + Paraffin (% released) | Cage Polymer + IMI Salt + Silicon oil (% released) |
| 9 | 0 | 0 | 0 | 12 | 10 |
| 10 | 0 | 0 | 0 | 6* | 6* |
| R | 4 | 5 | 6 | 10 | 10 |

Note:
UV absorbance of the wash solution was measure at 264 μm.
*Not all of the AI in the sample was released after 10 washings.

The final size of the flower foam +IMI acid+paraffin overcoating was varied between 2 and 75 μm. All sizes exhibited similar results in the polymer cage environment and coating that controlled the release of the AI. A variation on this technology is to combine an interface control ($IC_1$) polymer (polyvinyl acetate) with the IMI acid and absorb the combination, using dichloromethane as the solvent on to the flower foam followed by overcoating with hydrophobic polymer-like polystyrene ($IC_2$) and testing its controlled-release capabilities. These results are shown in Table 11.

TABLE 11

Example 2 Results [cage polymers + IMI acid ($INDP_1$)/polyvinyl acetate + polystyrene or paraffin ($IC_1$)]

| Number of Washings | Control (IMI acid alone) (% released) | Cage polymer + IMI acid/Polyvinyl acetate + polystyrene or paraffin (% released) Polystyrene | Paraffin |
|---|---|---|---|
| 1 | 28 | 19 | 17 |
| 2 | 30 | 20 | 21 |
| 3 | 25 | 15 | 18 |
| 4 | 13 | 11 | 13 |
| 5 | 4 | 9 | 8 |
| 6 | 0 | 7 | 7 |
| 7 | 0 | 7 | 5 |
| 8 | 0 | 5 | 4 |
| 9 | 0 | 2 | 3 |
| 10 | 0 | 2* | 2* |
| R | 5 | 10 | 10 |

*Not all of the AI in the sample was released after 10 washings.

Similar results were observed when the IMI acid was replaced with an amine (isopropyl) salt of 2,4D, as shown in Table 12.

TABLE 12

Example 2 Results [cage polymer + 2,4-D salt ($INDP_1$) + 6% paraffin ($IC_1$)]

| Number of Washings | 2,4-D Salt Content (% released) | 2,4-D Salt/Flower Foam Paraffin (% released) |
|---|---|---|
| 1 | 86 | 18 |
| 2 | 14 | 19 |
| 3 | 0 | 15 |
| 4 | 0 | 11 |
| 5 | 0 | 9 |
| 6 | 0 | 8 |
| 7 | 0 | 7 |
| 8 | 0 | 5 |
| 9 | 0 | 3 |
| 10 | 0 | 1* |
| R | 2 | 10 |

*Not all of the AI in the sample was released after 10 washings.

Other examples of 2,4-D in polymer cage ($INDP_1$) and interface control materials (silicone oils, Gantrez AN-169) are shown in Tables 13 and 14.

TABLE13

2,4-D Salt-polymeric Cage [(flower foam) interaction design parameter ($INDP_1$) and hydrophobic interface control ($IC_1$) samples]

| Number of Washings and R Values | 2,4-D Amine Salt (Control) (% released) | 2,4-D Salt in Less than 100 μm size Flower Foam ($INDP_1$) (% released) | 2,4-D Salt + Flower Foam + Hydrophobic (silicone oil) $IC_1$ Material (% released) |
|---|---|---|---|
| 1 | 94 | 36 | 18 |
| 2 | 6 | 36 | 18 |
| 3 | 0 | 18 | 15 |
| 4 | 0 | 4 | 11 |
| 5 | 0 | 4 | 10 |
| 6 | 0 | 1 | 8 |
| 7 | 0 | 1 | 6 |
| 8 | 0 | 0 | 5 |
| 9 | 0 | 0 | 3 |
| 10 | 0 | 0 | 2* |
| R | 2 | 7 | 10 |

*Not all of the sample was released after 10 washings.

TABLE 14

2,4-D Salt-polymeric Cage Interaction Design Parameter ($INDP_1$) and Hydrophilic Interface Control ($IC_1$) and Hydrophobic Materials ($IC_2$) Samples

| Number of Washings and R Values | 2,4-D Amine Salt (Control) (% released) | 2,4-D Salt + Gantrez AN-169 ($IC_1$) in Less than 100 μm Flower Foam ($INDP_1$) (% released) | 2,4-D Salt + Gantrez AN-169 ($IC_1$) in Flower Foam (<100 μm) ($INDP_1$) + hydrophobic paraffin oil ($IC_1$) (% released) |
|---|---|---|---|
| 1 | 94 | 30 | 0 |
| 2 | 6 | 25 | 5 |
| 3 | 0 | 15 | 6 |
| 4 | 0 | 8 | 6 |
| 5 | 0 | 6 | 7 |
| 6 | 0 | 5 | 8 |
| 7 | 0 | 3 | 24 |
| 8 | 0 | 3 | 18 |
| 9 | 0 | 1 | 15 |
| 10 | 0 | 1* | 10* |
| R | 2 | 10 | 10 |

*Not all of the sample was released after 10 washings.

Example 3

Self-Assembly Controlled Release Polymer-AI Interaction Design Parameter ($INDP_1$) and Interface Control ($IC_1$) Combinations In this disclosure, we have discovered that AI's and certain polymers (P) can form strong associations or complexes when combined together in a carrier solvent. These AI-P complexes when applied to and dried on a substrate (filter paper, plants, seeds, soils, or substrates) maintain some degree of their initial association properties, which strongly influences the controlled release of the AI in the presence of water or rain.

AI+polymer+carrier solvent[liquid AI-P initial complex or association]

[liquid AI-P initial complex or association]+Substrate [dried final Substrate-AI-P complex or association]

[dried final Substrate-AI-P complex or association]+ water (rain) controlled release of AI There are also other situations where the AI and polymer might not form a complex or association, but when applied to a substrate and dried, the special complex self-associates and produces a unique structure that controls the release rate of the AI in the presence of water or rain.

AI + P + carrier substrate —(Apply and dry on a substrate)→ [final dried AI—P-Substrate complex]

(no initial complex or association is formed in solution) (Complex is formed on drying)

[final dried AI-P-Substrate complex or association+ water (rain) controlled release of AI The different types of AI-polymer (P) combinations that can form these types of complexes or associations are described as follows:

Solvent soluble AI+solvent soluble polymer→[liquid AI-P complex]

Solvent soluble AI+dispersed polymer or oil→[liquid AI-P complex]

Dispersed AI+soluble polymer=[liquid AI-P complex]

Dispersed AI+dispersed polymer or oil→[liquid AI-P complex]

Dry AI+dry polymer→[dry AI-P complex]

[dry AI-P complex]+solvent→[liquid AI-P complex)

The following tables describe the self-assembly controlled-release systems of this disclosure.

In one formulation, 1 g of AN-179 (GANTREZ® methyl vinyl ether/maleic anhydride copolymer) was combined with 5 g of a solution of the isopropyl amine (IPA) neutralization salt of the IMI acid (23.6% IMI acid/12 g; 5.3% IPA/0.3 g; 71.1% water/3.5 g) to give a mixture that was 1.8% AN-179, 2.1% IMI acid; 0.5% amine and 95.6% water. In this example, the AN-179 is the interaction design parameter ($INDP_1$) and interface control ($IC_1$) polymer in one structure and the test results for this system are shown in Table 15.

TABLE 15

Self-assembly Controlled-release Polymer-AI Interaction Design Parameter ($INDPI_1$ and $IC_1$) Combinations

| Number of Washings | IMI Salt Content (% released) | AI + Gantrez (% released) |
|---|---|---|
| 1 | 100 | 41 |
| 2 | 0 | 31 |
| 3 | 0 | 10 |
| 4 | 0 | 5 |
| 5 | 0 | 5 |
| 6 | 0 | 2 |
| 7 | 0 | 2 |
| 8 | 0 | 1 |
| 9 | 0 | 1 |
| 10 | 0 | 0.5* |
| R | 1 | 10 |

*Not all of the AI in the sample was released after 10 washings.

The same self-assembly controlled release was observed with Dicamba amine salts using AN-169 (maleic anhydride vinyl ether copolymer or polyacrylic acid) as shown in Table 16.

TABLE 16

DICAMBA with a Combination $INDP_1$/$IC_1$ Polymer (AN-169 or polyacrylic acid)

| Number of Washings and R Values | Dicamba Salt Control) (% released) | Dicamba Salt + AN-169 or polyacrylic acid ($INDP_1$/$IC_1$) (% released) |
|---|---|---|
| 1 | 71 | 37 |
| 2 | 29 | 45 |
| 3 | 0 | 14 |
| 4 | 0 | 4 |
| 5 | 0 | 0 |
| R | 2 | 4 |

A variation of the self-assembly technology was to add 0.3 g of a water-soluble ammonium hydroxide zinc oxide (zincate) to 0.3 g of a water-soluble polyacrylic acid (Carbopol 716 NF) or AN-179 and 1.4 g of the water-soluble salt of the IMI acid (amine neutralized) in water. The mixture was placed on a filter paper substrate, dried and resulted in a zinc metal ion crosslinked structure with the polyacrylic acid. The crosslinked metal-organic hybrid structure immobilized the IMI salt, which resulted in a unique interface coated environment for controlled release of the AI (Table 17).

TABLE 17

Zinc-polyacrylic Acid Crosslinked Structure - IMI salt system $INDP_1$ and $IC_1$

| Number of Washings | IMI Salt Control (% released) | Zinc-Polyacrylic Acid Crosslinked Structure-IMI Salt System (% released) |
|---|---|---|
| 1 | 83 | 10 |
| 2 | 17 | 10 |
| 3 | 0 | 13 |
| 4 | 0 | 12 |
| 5 | 0 | 10 |
| 6 | 0 | 10 |
| 7 | 0 | 8 |
| 8 | 0 | 9 |

TABLE 17-continued

| Zinc-polyacrylic Acid Crosslinked Structure - IMI salt system $INDP_1$ and $IC_1$ | | |
|---|---|---|
| Number of Washings | IMI Salt Control (% released) | Zinc-Polyacrylic Acid Crosslinked Structure-IMI Salt System (% released) |
| 9 | 0 | 9 |
| 10 | 0 | 9 |
| R | 2 | 10 |

A critical processing step is sometimes required to create the AI-polyacid $INDP_1$: $IC_1$ complex or association. The AI and the polyacid can be mixed together as 100% dry solids with a small amount of water and rolled overnight to form the associated controlled-release product. After the association is formed, then the mixture can be diluted with water for spray application at which time, the complex reassembles upon drying on the filter paper or interacting with the soil and subsequent removal (drying) of the water carrier.

If the AI and the polyacid are mixed together in solution, the complex might not be formed and the AI/polyacid solution applied to the filter paper and dried might release the AI in the presence of the polyacid at almost the same rate as the AI applied to the filter paper alone (control) and washed with ten 10-mil aliquots of water.

The AN-179 maleic acid-alkyd vinyl ether copolymers are unique in that both the maleic acid and the alkyl vinyl ether structures of the polymer can form a strong association with the AI($INDP_1$/$INDP_2$). The acid functions, however, can be neutralized with base, interact with water, or react with soil, which then becomes the $IC_1$ element that controls the release of the AI (See FIG. 9). Any water soluble/dispersible polymer in combination with a water soluble/dispersible crosslinking agent that is stable in solution/dispersion, but upon application to a substrate and drying into a crosslinked structure to control the release of an AI, is subsumed within the present disclosure.

Pyriproxyfen is a water insoluble (0.37 mg/l) AI with a log P of 5.37 and Kd values of 637 and Koc values of 58,000 for clay-loam soils (McGinniss Equation, $\chi_N$0.044 and $\chi_O$=0.15). Pyriproxyfen shows no mobility on filter paper or soil and washed with several 10 ml aliquots of water. When pyriproxyfen (PPF) is combined with $INDP_1$ surfactants like Tween 20 or Pluronic 25 R2 (HLB=7-16, log P=−0.74 to 1.5, $\delta_d$=8-10, $\delta_1$, $\delta_h$=7-11; McGinniss $\chi_o$=0.3-0.34) these compounds allow the PPF to be easily transported through filter paper and soil as shown in the following table:

TABLE 18

| Self Assembly AI Hi $K_{OC}$ (Pyriproxyfen) Filter Paper/Soil Release System | | | |
|---|---|---|---|
| Number of Washings | Pyriproxyfe (PPF) Control (% Released) | PPF + $INDP_1$ (Pluronic 25 RS) (% Released) | PPF + $INDP_1$ (Tween 20) (% Released) |
| 1 | 0 | 50 | 50 |
| 1 | 0 | 30 | 30 |
| 3 | 0 | 10 | 10 |

The number of washings are the same as the other examples (10 ml aliquots of water) the pure AI PPF just sat on the filter paper or the soil and did not move with any of the water washes; hence, no controlled release. It was only when we used 70% PPF with 30% of a surfactant (Tween 20 or Pluronic 25) having the right HLB and log P and McGinniss $\chi$ parameters did it become solubilized and move off the soil or the filter paper.

Example 4

Hydrophilic/Hydrophobic Polymer-AI Interaction Design Parameter ($INDP_1$) Interface Control ($IC_1$) Combinations In this example, 2 g of the IMI acid was added to 7 g (50/50 by weight) of a hydrophilic polymer (vinyl acetate/acrylic copolymer ROVACE™ 9900 emulsion, Rohm & Haas #10078657) ($INDP_1$) and a hydrophobic polymer (Satin-Lok® silicon/acrylic polymer emulsion Rain Guard Weatherman Product Inc.) ($IC_1$) to give a composition that was 27.2% IMI acid, 38.9% polyvinyl acetate (21.4% solids), and 38.9% silicone polymer (9.7% solids).

The results for this latex blend system and polyvinyl acetate latex alone and a polysilicone hydrophobic emulsion alone are shown in Table 18.

TABLE 18

| Example 4 Results (hydrophilic/hydrophilic-IMI acid) | | | | |
|---|---|---|---|---|
| Number of Washings | IMI Acid Control (% released) | Polyvinyl Acetate Latex/ IMI acid) (% released) | Hydrophilic/ Hydrophobic- IMI Acid (% released) | Hydrophobic- IMI Acid (% released) |
| 1 | 41 | 25 | 13 | 40 |
| 2 | 37 | 20 | 9 | 30 |
| 3 | 14 | 18 | 9 | 20 |
| 4 | 5 | 15 | 10 | 5 |
| 5 | 0 | 10 | 10 | 5 |
| 6 | 0 | 6 | 10 | 0 |
| 7 | 0 | 6 | 9 | 0 |
| 8 | 0 | 0 | 10 | 0 |
| 9 | 0 | 0 | 9 | 0 |
| 10 | 0 | 0 | 8* | 0 |
| R | 4 | 6 | 10 | 5 |

*Not all of the AI in the sample was released after 10 washings.

The results in Table 18 indicate that a balance needs to be created between the $INDP_1$ hydrophilic (polyvinyl acetate latex) and the hydrophobic (silicone/acrylic latex, $IC_1$) in order to achieve good controlled-release properties of the AI.

Example 5

Comparison Between Filter Paper Test and Soil Test for 2,4-D Amine Salt and Latex Blends Table 19 shows the results of applying a 2,4-D amine salt solution (23.5 g 2,4-D acid, 5.5 g isopropyl amine, and 71.0 g DI water) control onto filter paper and 28.4 μl of the control solution onto a soil column, drying, and washing with water. The soil column was prepared by cutting off the tip of a 15 ml VWR brand CAT, No. 20171-036 polypropylene centrifuge tube leaving approximately a ⅛-inch opening, which was filled with cotton to prevent the soil from pouring out the bottom. The cotton block was 0.5-inch thick, which held unpacked 3 inches of Nature's topsoil from the Michigan Peat Co., (Oakland Nursery). The topsoil was sieved ten times through a #7 metal screen sieve to remove large debris before filling the tubes.

The other samples that were applied to both the filter paper and then topsoil were a mixture of 2,4-D amine salt and the Rain Guard/Rovace 9900 latex blend to form a sample that was 14.7% 2,4-D amine salt, 21.4% Rain Guard, and 64% Rovace 9900. A 50-μl sample of the mixture was applied to the filter paper and dried while a 200-μl sample was applied to the top of the soil columns and dried before washing with ten 10-ml aliquots of water.

The information contained in Table 19 confirms that the controlled-release performance of the AI-polymers of this disclosure on a filter paper screening test correlates with the same samples applied to the soil column test as well. A listing of some commercial latex polymers that can be used in this disclosure are shown in Table 20.

TABLE19

Comparison between Filter Paper and Soil Testing for 2,4-D Amine Salts and Interaction Design Parameter ($INDP_1$) and Interface Control ($IC_1$) Polymers

| Number of Washings and R Values | 2,4-D Amine Salt (Control on filter paper) (% released) | 2,4-D Amine Salt + Latex Blend on Filter Paper (% released) | 2,4-D Amine Salt (Control) or Soil Column (% released) | 2,4-D Amine Salt + Latex Blend on Soil (% released) |
|---|---|---|---|---|
| 1 | 94 | 14 | 32 | 12 |
| 2 | 6 | 13 | 26 | 16 |
| 3 | 0 | 13 | 20 | 16 |
| 4 | 0 | 10 | 13 | 14 |
| 5 | 0 | 10 | 9 | 12 |
| 6 | 0 | 11 | 0 | 10 |
| 7 | 0 | 7 | 0 | 10 |
| 8 | 0 | 10 | 0 | 10 |
| 9 | 0 | 9 | 0 | 0 |
| 10 | 0 | 2* | 0 | 0 |
| R | 2 | 10 | 5 | 8 |

*Not all of the sample was released after 10 washings.

| |
|---|
| H. G. Fuller |
| National Rubber latexes<br>Rhodia PPMC |
| Dispersions based on vinylacetate homopolymers (plasticized, non plasticized), vinylacetate maleic ester copolymers, vinylacetate versatate copolymers, acrylic esters, styrene butadiene copolymers, carboxylated butadiene copolymers (Rhodopas), styrene acrylic copolymers (Rhoximat).<br>Elotex AG |
| Dispersions based on vinylacetate vinylversatate copolymers, vinylacetate ethylene copolymers as well as pure acrylic dispersions.<br>F.A.R. Fabbrica Adesivi Resine S.p.A. |
| Polymer dispersions based on PVAc homopolymer, PVAc copolymers, acrylics and styrene-acrylics. (Neolith) Located in Italy.<br>Prochem AG |
| Distributor of polymer dispersions (manufactured by Dow Chemical) to the Swiss market.<br>Dairen Chemical Corporation (DCC) |
| Polymer emulsions based on vinyl acetate-ethylene copolymers and vinyl acetate-ethylene-acrylate terpolymers. Located in Taiwan.<br>BCD Rohstoffe für Bauchemie HandelsGmbH |
| A family of pure acrylic and styrene acrylic dispersions. (Chemco ®, Vinagen ®)<br>Dow Reichhold Specialty Latex LLC |
| Styrene-Butadiene (SB) Latex and VAE/Acrylic/Copolymer emulsions.<br>CSC Jäklechemie GmbH & Co. KG (German) |
| Latices produced by Bayer AG (i.e., Baypren ®).<br>Rohm and Haas |
| Acrylic, styrene acrylic and vinyl acrylic, vinyl acetate-acrylic copolymers, vinyl acetate homopolymer emulsions. (Paraloid ®, Res ®, Rhoplex ®, RoShield ®)<br>Vinamul Polymers |
| Synthetic polymer emulsions based on ethylene vinyl acetate (EVA) and polyvinyl acetate (PVA).<br>Hüttenes-Albertus Lackrohstoff GmbH |
| Wide range of emulsions based on acrylate and polyurethane and combinations of both. Physically drying, external- and self-crosslinking, oxidatively curing, UV-curable. |

-continued

| |
|---|
| Crompton Corporation |
| Witcobond ® polyurethane dispersions provide coating and adhesive properties for use on wood, plastics, leather, and rubber. |
| C.H. Erbslöh KG |
| Supplies Alberdingk products: Dispersions based on homopolymers and copolymers of acrylate, methacrylate esters, styrene, vinylacetate and maleinic acid di-n-butyl ester. |
| Paramelt B.V. |
| Waterbased dispersions based on unplasticized, solvent free, high molecular weight thermoplastic ethylene copolymers. These products are aqueous ammoniacal or alkali metal dispersions and have been developed for packaging and industrial applications which require clear (heat scalable) polymer coatings. (Aquaseal) |
| BASF Aktiengesellschaft |
| Polymer dispersions based mainly on momomers like acrylic acid and acrylic esters. Trade names are: Acronal, Styrofan, Butofan, Butonal, Acrodur und Luphen. |
| Dynea |
| Produces polymer dispersions for the formulation of adhesives, paints and plasters. (Dilexo) |
| Celanese AG |
| Mowilith ® emulsions for industries like construction, adhesive and paint. |
| Industrial Copolymers Ltd. |
| Polyurethane Dispersions (aliphatic polyurethanes). (Incorez ®) |
| Wacker Chemie AG |
| Water-borne emulsions based on vinyl acetate and its binary copolymers and/or terpolymers. (Vinnapas) |
| Polvmer Latex GmbH & Co. KG |
| Polymer dispersions from various polymer classes: Polychloroprene rubber, styrene-butadiene-rubber, pure acrylic, styrene acrylate copolymer, carboxylated styrene butadiene rubber, polyurethane. Trade names are: Acralen, Baypren, Baystal, Lipaton, Perbunan, Plextol, Pyratex, Rohagit. |
| Acquos |
| Manufactures redispersible polymers for the dry mortar industry as well as acrylic emulsion polymers for mortars and construction coatings. Located in Australia. |
| Synthomer GmbH |
| Dispersions based on polyvinyl acetates (homopolymers, copolymers), acrylic polymers homopolymers and copolymers) and styrene butadiene latex (SBR and Nitrile). |
| Johnson Polymer |
| Acrylic emulsions, polyurethane and polyurethane hybrid emulsions. |
| Jesons Industries Ltd. |
| Polymer emulsions based on acrylates, acrylate co-polymers, and vinyl acetate co-polymers. Located in India. |

In this disclosure, we have used a combination of different latex polymers as blends or hybrid polymer latexes with AI's and observed very controlled release results. The hybrid latex technology is described below.

Hybrid polymer latexes can be defined as colloidal dispersions in which at least two distinct polymers exist within each particle. The two polymers can form a homogeneous blend within the particles or a nano to microphase separation of the polymers can also occur. These latexes can be prepared in the following manner:

1) The first polymer is prepared by polycondensation or polyaddition and added to mixtures of unsaturated monomers to form nano or micron size emulsions under high shear and then free radically polymerized to create the system.
2) A seeded emulsion polymerization of unsaturated monomers is used where the polycondensate is the seed in the emulsion polymerization process. The polycondensate can be vegetable oils, alkyd resins, proteins, polyesters, epoxy resin, polyurethanes, silicones, or other polymers.

A full description or how to prepare these hybrid polymer latexes can be found in Progress in Polymer Science, Vol. 32 (2007) 1439-1461; WO/2009/146252 and WO/2005/121222.

Example 6

AI-Polymer and Other Material Soil Interactions

The interaction of an AI and polymers or other materials (e.g., surfactants, oils, fillers) with soil is a complicated process. Soil compositions range from sand (low or 0 to 10% clay content) to loam (8 to 28%) and soils with 40 to 100% clay content. Jerome B, Weber, et al. published and excellent treatise, "Calculating Pesticide Sorption Coefficients ($K_d$) Using Selected Soil Properties" [Chemosphere, Vol. 55, (2009), pp 157-166], where 57 pesticides (carboxy acid, amino sulfonyl acid, hydroxy acid, weakly basic compounds and nonionizable amide/anilide, carbamate, dinitroaniline, organochlorine, organophosphate, and phenylurea compounds.) and their $K_d$ values were correlated with the organic matter (OM) content, clay (Cl) content and pH of the soil.

In general, the $K_d$ values for AI's that contain carboxylic acids or $NHSO_2$ acid functionality are highly correlated with the OM content and/or pH in the soil and sorption of these AI's increased as the OM content increased and/or as pH decreased.

Weak base pesticides $k_d$ values were related to one or more of the three soil properties (OM, Cl, pH) and sorption increased as OM and/or Cl increased and/or pH decreased. Nonionizable pesticides $k_d$ values were strongly related to OM and/or Cl content of the soil and increased or decreased as the concentration of the OM and Cl were varied in a similar manner. Tables 21, 22, 23, 24, and 25 contain the $K_d$ values for the different classes of AI's and their relationship to the soil properties (OM, pH, Cl) that are a significant influence on the AI's discussed in the Webber article. Other AI information (water solubility, log P, and $K_{oc}$) was obtained from the EMA/EMA online pesticide properties database (IUPAC Footprint Pesticides Procedures Database; (http:\\sitem.herts.ac.UK/aeris/ipac/442.htm). Also included in the tables are the McGinniss Equation $\chi$ parameters for the oxygen, nitrogen, sulfur, and phosphorus elements contained in the active ingredients.

All of the variables in the tables can be used to determine which properties of the AI's and their molecular/atomic structures control their ability to interact with $K_{oc}$ and $K_d$ soil sorption values.

Multiple linear regression analysis of the data in Table 21 (carboxylic acid-containing AI's) show that there is no direct correlation between $K_d$ and $K_{OC}$ (K=0.04). There is, however, a strong correlation of $K_d$ with the McGinniss Equation parameters $\chi$o, $\chi$n, and log P(R=0.90).

The $K_{OC}$ values for the AI's in Table 21 are also correlated with their water solubilities, $\chi$n, and log P values (R=0.90) and the log of the water solubilities for the AI's are somewhat correlated with the $\chi$n and $\chi$o parameters (R=0.82).

From this type of information, one can select polymer structures that have similar or different log P, or solubility parameters with water sensitivities, $\chi_O$ and $\chi_N$ parameters and functional groups (carboxylic acids) that can interact either strongly or weakly with the AI and the soil to maximize or minimize the effects that control the release of the AI from the AI-polymer-soil matrix. It should be noted that the dispersion, polar, and hydrogen bonding solubility parameter values for the AI's in Table 21 showed no correlation (R=0 to 0.40) with $K_{oc}$. The solubility parameter values for these AI's were determined from the solvents (acetone, methanol, toluene, or ethyl acetate) in which they were soluble.

Table 22 lists the properties of various sulfur-containing AI's; with these compounds there is no direct correlation with $K_d$ or $K_{OC}$. The variable $K_d$ is correlated with the McGinniss Equation $\chi$o, $\chi$n parameters and log of the water solubility (R=0.89); and the log $K_{OC}$ is correlated with $\chi$s, water solubility value and the log of the water solubility value (R=0.89). The log P for these AI's is slightly correlated with the $\chi$o, $\chi$n, and $\chi$s parameters (R=0.85).

Table 23 lists the parameters for the weak base AI's and with the sulfur weak base AI's, $K_d$ was correlated with their water solubility (R=0.91), log P was correlated with $\chi$s (R=0.94) and there was no direct correlation relating $K_d$ with $K_{OC}$. The $K_{oc}$ values for these AI's, however, are slightly correlated with $\chi_N$ and the log of the water solubility values (R=0.87).

The remainder AI's in Table 23 (sulfur AI compounds excluded) do show a direct correlation with $K_d$ and $K_{OC}$ (R=0.95), while the log of $K_{OC}$ correlated with $\chi$o, $\chi$n and the water solubility of the AI's (R=0.90). Log P is slightly correlated with $\chi$n, the water solubility and log of the water solubility value of the AI's (R=0.82).

Table 24 contains the properties for urea type AI's; these compounds do have a direct correlation with $K_d$ and $K_{OC}$ (R=0.99) and the log of $K_{OC}$ is highly correlated with $\chi$o and the log of the water solubilities for the AI's (R=0.95) as is log P for the same variables (R=0.93).

Similar correlations can be made for the phosphorous containing AI's in Table 25, where there is a slight direct correlation between $K_d$ and $K_{OC}$ (R=0.82), and $K_d$ can be slightly correlated with $\chi$o, the water solubility of the AI's and the log of the water solubility (R=0.87), while the log of $K_{OC}$ and log P can be correlated with the same variables (R=0.93 and R=0.92, respectively).

TABLE 21

Carboxylic Acid-containing Active Ingredients (AI's)

| Active Ingredient (AI) | $\chi_O$ | $\chi_N$ | Water Solubility (mg/l) | Log P | $K_{OC}$ | $K_d$ |
|---|---|---|---|---|---|---|
| Quinclorac | 0.132 | 0.06 | 0.065 | −1.15 | 50 | 1.24 (OM) |
| Picloram | 0.13 | 0.12 | 560 | −1.92 | 35 | 0.47 (pH) |
| Imazethapyr | 0.166 | 0.145 | 1400 | 1.49 | 52 | 1.13 (pH) |
| Imazaquin | 0.152 | 0.135 | 102000 | −1.09 | 18 | 0.81 (OM) (pH) |
| 1-Napthylacetic Acid | 0.172 | 0 | 420 | 2.24 | 385 | — |
| Dicamba | 0.217 | 0 | 250000 | −1.88 | 12 | — |
| 2,4-D | 0.217 | 0 | 23180 | −0..83 | 56 | 0.49 (pH) |

$\chi_O$ and $\chi_N$ are the McGinniss Equation parameters for oxygen and nitrogen contained in the AI.

TABLE 22

| Various Sulfur-containing Active Ingredients (AI's) | | | | | | | |
|---|---|---|---|---|---|---|---|
| Active Ingredient (AI) | $\chi_O$ | $\chi_N$ | $\chi_S$ | Water Solubility (mg/l) | Log P | $K_{OC}$ | $K_d$ |
| Flumetsulam | 0.098 | 0.215 | 0.098 | 5650 | 0.21 | 28 | 2.88 (OM)(pH) |
| Fomesafen | 0.219 | 0.064 | 0.073 | 60 | −1.2 | 50 | 4.52 (OM)(pH) |
| Sulfentrazone | 0.124 | 0.145 | 0.083 | 780 | 1 | 43 | — |
| Triflusulfuron-Methyl | 0.195 | 0.171 | 0.065 | 260 | 0.96 | 40 | 0.78 (OM) |
| Sulfometuron-Methyl | 0.219 | 0.154 | 0.09 | 70 | −0.51 | 85 | 0.97 (OM)(CI)(pH) |
| Chlorsulfuron | 0.179 | 0.196 | 0.09 | 12500 | −0.99 | 36.3 | 0.69 (pH) |
| Tribenuron-Methyl | 0.243 | 0.177 | 0.081 | 2040 | 0.78 | 31 | 1.08 (pH) |
| Rimsulfuron | 0.26 | 0.162 | 0.148 | 7300 | −1.46 | 47 | 0.87 (pH) |
| Primisulfuron | 0.246 | 0.123 | 0.07 | 70 | 0.2 | 50 | 0.17 (pH) |

$\chi_O$, $\chi_N$, and $\chi_S$ are the McGinniss Equation parameters for oxygen, nitrogen, and sulfur contain in the AI.

TABLE 23

| Weak base-containing Active Ingredients (AI's) | | | | | | | |
|---|---|---|---|---|---|---|---|
| Active Ingredient (AI) | $\chi_O$ | $\chi_N$ | $\chi_S$ | Water Solubility (mg/l) | Log P | $K_{OC}$ | $K_d$ |
| Anilazine | 0 | 0.2 | 0 | 8 | 3.02 | 2000 | 20.6 (pH) |
| Hezazinone | 0.127 | 0.222 | 0 | 33000 | 1.17 | 54 | 0.45 (OM)(pH) |
| Propiconazole | 0.09 | 0.123 | 0 | 150 | 3.72 | 1086 | 6.27 (OM)(CI) |
| Thiabendazole | 0 | 0.209 | 0.159 | 30 | 2.39 | 2500 | 9.55 (OM)CI)(pH) |
| Triadimenol | 0.108 | 0.142 | 0 | 72 | 3.18 | 273 | 3.89 (OM)(pH) |
| Tricyclazole | 0 | 0.223 | 0.169 | 596 | 1.4 | 169 | 23 (CI) |
| Ametryn | 0 | 0.308 | 0.141 | 200 | 2.63 | 316 | 5.69 (OM)(pH) |
| Atrazine | 0 | 0.324 | 0 | 35 | 2.7 | 100 | 2.65 (OM)(CI)(pH) |
| Cyanazine | 0 | 0.349 | 0 | 171 | 2.1 | 190 | 2.46 (OM)(pH) |
| Prometon | 0.071 | 0.311 | 0 | 620 | 2.91 | 150 | 4.86 (CI)(pH) |
| Prometryn | 0 | 0.29 | 0.133 | 33 | 3.34 | 400 | 7 |
| Propazine | 0 | 0.305 | 0 | 8.6 | 3.95 | 154 | 2.09 |
| Simazine | 0 | 0.347 | 0 | 0.5 | 2.3 | 130 | 2.19 |
| Terbutryn | 0 | 0.29 | 0.133 | 22 | 3.65 | 2000 | 6.75 |

$\chi_O$, $\chi_N$ and $\chi_S$ are the McGinniss Equation parameters for oxygen, nitrogen, and sulfur contained in the AI.

TABLE 24

| Urea-containing Active Ingredients (AI's) | | | | | | |
|---|---|---|---|---|---|---|
| Active Ingredient (AI) | $\chi_O$ | $\chi_N$ | Log P | $K_{OC}$ | Water Solubility (mg/l) | $K_d$ |
| Diuron | 0.07 | 0.12 | 2.87 | 1067 | 35.6 | 7.37 (OM) |
| Nicosulfuron | 0.23 | 0.2 | 0.61 | 21 | 7500 | 0.69 (pH) |
| Fenuron | 0.1 | 0.17 | 0.98 | 42 | 3850 | 0.76 (OM) |
| Fluometuron | 0.07 | 0.12 | 2.28 | 67.4 | 111 | 0.99 (OM) |
| Monuron | 0.08 | 0.14 | 1.79 | 150 | 230 | 2.04 (OM) |
| Isoproturon | 0.08 | 0.13 | 2.5 | 122 | 70.2 | — |
| Lufenuron | 0.09 | 0.05 | 5.12 | 41182 | 0.046 | — |
| Linuron | 0.13 | 0.112 | 3 | 620 | 63.8 | — |
| Neburon | 0.06 | 0.1 | 3.8 | 2500 | 4.8 | 89.7 (OM) |
| Siduron | 0.07 | 0.12 | 2.7 | 420 | 18 | — |
| Thidiazuron | 0.07 | 0.25 | 1.77 | 742 | 20 | — |
| Chlorimuron-Ethyl | 0.23 | 0.13 | 0.11 | 106 | 1200 | 1.1 (OM)(pH) |

$\chi_O$ and $\chi_N$ are the McGinniss Equation parameters for oxygen and nitrogen contained in the AI.

TABLE 25

| Phosphorus-containing Active Ingredients (AI's) | | | | | | | | |
|---|---|---|---|---|---|---|---|---|
| Active Ingredient (AI) | $\chi_O$ | $\chi_N$ | $\chi_S$ | $\chi_P$ | Water Solubility (mg/l) | Log P | $K_{OC}$ | $K_d$ |
| Azinphosmethyl | 0.15 | 0.13 | 0.2 | 0.097 | 28 | 2.96 | 1000 | 8.94 (OM) |
| Chlorethoxyfos | 0.143 | 0 | 0.095 | 0.092 | 0.1 | 3.97 | 6100 | 63.2 (OM) |
| Dicrotophos | 0.337 | 0.006 | 0 | 0.131 | 100000 | −0.5 | 75 | 1.01 (OM) |
| Dimethonate | 0.21 | 0.006 | 0.279 | 0.135 | 398000 | 0.704 | 30 | 0.45 (OM) |
| Disulfuton | 0.12 | 0 | 0.35 | 0.113 | 25 | 3.95 | 13454 | 14.7 (OM) |
| Fenamiphos | 0.158 | 0.46 | 0.105 | 0.102 | 345 | 3.3 | 754 | 3.84 (OM) |
| Fenthion | 0.17 | 0 | 0.23 | 0.111 | 4.2 | 4.84 | 1500 | 18.2 (OM) |
| Iodufenphos | 0.12 | 0 | 0.08 | 0.075 | 0.1 | 5.51 | 50000 | — |
| Parathion | 0.275 | 0.05 | 0.11 | 0.106 | 12.4 | 3.83 | 7660 | 26 (OM) |
| Isazofos | 0.153 | 0.134 | 0.102 | 0.099 | 69 | 3.1 | 155 | 1.48 (OM) |
| Phorate | 0.123 | 0 | 0.369 | 0.112 | 50 | 3.86 | 1660 | 6.47 (OM) |
| Piperophos | 0.136 | 0.04 | 0.18 | 0.088 | 25 | 4.3 | 5202 | 31.8 (OM) |
| Profenofos | 0.128 | 0 | 0.086 | 0.083 | 28 | 1.7 | 2016 | 22 (OM)(CI)) |
| Trichlorfon | 0.249 | 0 | 0 | 0.12 | 120000 | 0.43 | 10 | 0.27 (OM)(CI) |
| Glyphosate | 0.476 | 0.08 | 0 | 0.18 | 10500 | −3.2 | 21699 | — |

Where $\chi_O$, $\chi_N$, $\chi_S$, and $\chi_P$ are the McGinniss Equation parameters for oxygen, nitrogen, sulfur, and phosphorus in the AI.

The information discussed in Tables 21 through 25 allows one to design polymer systems (INDP and $C_1$) that are specifically matched for controlling the release of an AI in different types of soil. For example, AI's with $K_{OC}$ (μg/g) values is the 2 to 99 range are weakly bonded to OM soils while AI's with $K_{OC}$ values of 100 to 999 and $1000^+$ tend to have moderate or extensive interaction with the soil and do not migrate far from their application area (Table 26). The same argument can be made for AI's with low, medium and high $K_d$ values (0.1 to 10 to $100^+$) for the different types of mils (OM, pH, Cl) (Table 27).

TABLE 26

| AI-$K_{OC}$ -Soil Property Relationships | |
|---|---|
| AI | $K_{OC}$ (mg/g) |
| DICAMBA | 2 |
| 2,4-D | 20 |
| Metalaxyl | 50 |
| Tebuthiuron | 80 |
| Linuron | 400 |
| Terbufos | 500 |
| Diazinon | 1000 |
| Chlorpyrifos | 6,000 |
| Glyphosate | 24,000 |
| Paraquat | 1,000,000 |

SCS/ARS/CES, USDA, Pesticide Properties Database for Environmental Decision Making, Aug. 10, 1994.

TABLE 27

| AI, $K_d$-Soil Property Relationships | |
|---|---|
| Pesticide Type | Primary $K_d$ Interaction Parameters |
| Carboxylic acids | pH, OM |
| $NHSO_2$ acids | pH, OM |
| OH acids | OM |
| Weak bases | OM, pH, Cl |
| Nonionizable amidelamidides | OM |
| Carbamates | OM, Cl |
| Nitroanilines | OM, Cl |
| Organochlorides | OM |
| Phosphates | OM, Cl |
| Phenylurea | OM |

If a carboxylic acid AI has high transport through an OM type of soil (both $K_d$ and $K_{OC}$ are small), then an ideal controlled-release polymer should have a very high INDP interaction capacity with the AI and a very high interaction capacity and interface control functionality to interact with the soil when applied and dried, but should slowly release the AI in the presence of rain.

Highly water-sensitive or water-soluble nonionic or carboxylic acid/salts AI's complex with polymers that contain carboxylic and functionality. The types of polymers of this disclosure for water-soluble AI's can be described as follows:

$[A]_n$-

$[A\text{-}B]_n$-

$[A]_n$-[B$+_n$-

$[A]_n$-$[B\text{-}]_n$-$\underline{C}+_n$- where,

A=COOH containing monomers

B=hydrophilic or hydrophobic monomer

C=hydrophilics or hydrophobic monomer

The types of polymer for this disclosure for base sensitive AI's are as follows:

$[A]_n$-

$[A\text{-}B]_n$-

$[A]_n$-$[B]_n$-

$[A]_n$-$[B]_n$-$[C]_n$- where A=amine, triazine, or pyridine containing monomers

B, C=hydrophilic or hydrophobic monomers

Example 7

Emulsions, Dispersions, and Wettable Powders

A general description of an AI in an oil-in-water emulsion is shown in FIG. 10. A similar analogy can be made for AI's in a water-in-oil emulsion or an AI wettable powder (FIGS. 11, 12, and 13).

In FIG. 11, $INDP_1$ and $IC_1$ can be surfactants or water-soluble/dispersible polymers that keep the emulsion stable but influence the way the AI is transported through the soil or plant surfaces. Materials (polymers/surfactants) or fillers associated with the OECS controls the outside interface during storage and release upon application to the soil or plant surfaces.

In FIG. 12, $INDP_1$ materials (surfactants or polymers) keep the AI (solid/liquid) suspended in water while $IC_1$ materials (surfactants or polymers) controls the stability and release capabilities of the systems while in storage and after applied to soil or plant surfaces. The OECS materials (surfactants/polymers or fillers) maintain the stability of the AI water suspension in the oil phase but also control the release of the system when applied to soils or plant surfaces.

In FIG. 13, $INDP_1$ materials (polymers, surfactants, inorganic fillers) maintain the particle sizes of the system in a dry form and when the powders are dissolved or dispersed into water for limited storage and preparation time before application.

$IC_1$ materials (polymer, surfactants) protect the AI system from destabilization when dispersed into water, but also control the AI release and transport capabilities of the AI through the soil or plant surfaces.

$INDP_1$ and OECS materials (polymers/surfactants/fillers) protect the AI powder system from decomposition in water but at the same time, allow the powder to be wetted and dispersed into water, which then can be applied to soil/plant surfaces and release the AI in a controlled manner.

It should also be noted AI powder with $INDP_1$, $IC_1$, and OECS stabilization and controlled-release capabilities can be applied directly to soils or plant surfaces for a number of agricultural plant protection applications as well.

Example 8

Dendrimers

Dendritic polymers or dendrimers are highly branched polymers and are described in “Dendritic Molecules: Concepts, Synthesis Perspective,” G. Newkome, et al., John Wiley & Sons, 1986 and U.S. Pat. No. 6,379,683B1.

A number of poly(amido amine) PAMAM dendrimers are commercially available from SIGMA0Aldrich, 5050 Spruce Street, St. Louis, Mo. 63103, and Nanotechnologies, Inc. (dnanotech.com). Other references that describe dendrimers are Macromolecules 2001, 34, 4927-4936 and U.S. 2002/0045714 A1.

In this disclosure a PAMAM-succinamic acid dendrimer (10% in water) from Aldrich (592307-2G) was combined with the isopropyl amine salt of 2,4-D and placed on filter paper to dry. This sample was washed with the 10-ml aliquots of water and exhibited similar controlled-release properties as the 2,4-D acrylic acid or copolymers of methylvinyl ether/maleic anhydride materials. The control (2,4-D amine salt) was washed immediately through the filter paper in 1-2 washes and had no control release capabilities.

Example 9

AI Encapsulated (Micron to Nanosize Particles) (Cores or Core/Shells)

The conventional way of making micron to nanosize capsules of AI materials by an emulsion polymerization process can be described as follows:

1) Combine the vinyl monomers (acrylic or methacrylic esters) with a free radical initiator and the AI, which is then added to a water/surfactant solution, which is slowly dispersed while stirring. Slow mechanical mixing gives large particle size, while ultrasonic mixing can produce particle sizes in the nanometer size range. Heating up the water-monomer/initiator and AI materials causes the polymerization reaction to occur and create the micro or nanosize polymer encapsulated AI core material.
2) Obtain a core/shell product by taking the AI-nano- or micron-size core capsules (seeds) and placing them into a water solution of a surfactant and adding a second monomer (styrene or other acrylic acid esters) and an initiator to start the second polymerization reaction, which overcoats the original AI-polymer structure to form a core/shell product [Macromolecules 2004, 37, 7979-7985; U.S. Pat. No. 6,271,898 B1; journal of microencapsulation, September 2005, 22(6):683-688; nanoscale, 2010, 2, 829-843; progress in polymer science 33 (2008) 1088-1118 and Vol. 23 (1988), No. 8 pp 1383-1408; US2005/0226934 A1; U.S. Pat. No. 6,955,823 B2; U.S. 2003/0147965 A1 and Chinese Chemical Letters vol. 7, no. 2 pp 247-250 (2006)].

One difference between the prior art and the disclosure is that the prior art does not create an ideal environment for the AI-polymer matrix as it pertains to an enhanced control system under a variety of different environments exposure conditions.

In this disclosure, a nanosize polymer-AI seed or core structure was prepared by standard emulsion polymerization methods using ultrasonic agitation polymerization reactions of styrene (70% by weight), trichloroethylmethacrylate (23% by weight) and 5% by weight 2,4-D in water containing 0.5% sodium lauryl sulfate, 0.5% of anonionic surfactant (Tween 20), and a thermal initiator (1% by weight ammonium persulfate). This mixture was heated to 60 to 70° C. for 6 hours and resulted in a core that was hard and stable with particle sizes in the 200 to 500 nm size range.

This core seed polymer emulsion was split into two flasks and a polymer shell of styrene was polymerized over one of the polystyrene-AI core samples while a copolymer of styrene (50% by weight), methylmethacrylate (45%) and 5% methacrylic acid was polymerized over the other polystyrene-AI core material. The shell acts as both an $IC_1$ and an $OCES_1$ interface. The controlled release of the 2,4-D from these two samples are shown in Table 28.

TABLE 28

CORE SHELL ENCAPSULATION OF TWO SAMPLES

| Number of Washings and R Values | Polystyrene ($INDP_1$) 2,4-D core/ no $IC_1$ Component (% released) | Polystyrene ($INDP_1$) 2,4-D core; Polystyrene Shell($INDP_2$)/ no $IC_1$ or $IC_2$ Component (% released) | Polystyrene ($INDP_1$) 2,4-D core; Copolymer of polystyrene/ polymethylmethacrylate/ shell of polymethacrylic acid ($INDP_1$ and $IC_2$ and $OCES_1$ (% released) |
|---|---|---|---|
| 1 | 0 | 0 | 0 |
| 2 | 0 | 0 | 1 |
| 3 | 0 | 0 | 3 |
| 4 | 0 | 0 | 10 |
| 5 | 0 | 0 | 11 |
| 6 | 0 | 0 | 11 |
| 7 | 0 | 0 | 12 |

TABLE 28-continued

| CORE SHELL ENCAPSULATION OF TWO SAMPLES | | | |
|---|---|---|---|
| Number of Washings and R Values | Polystyrene ($INDP_1$) 2,4-D core/ no $IC_1$ Component (% released) | Polystyrene ($INDP_1$) 2,4-D core; Polystyrene Shell($INDP_2$)/ no $IC_1$ or $IC_2$ Component (% released) | Polystyrene ($INDP_1$) 2,4-D core; Copolymer of polystyrene/ polymethylmethacrylate/ shell of polymethacrylic acid ($INDP_1$ and $IC_2$ and $OCES_1$ (% released) |
| 8 | 0 | 0 | 9 |
| 9 | 0 | 0 | 10 |
| 10 | 0 | 0 | 12 |
| R | 0 | 0 | 10 |

These samples were applied to filter paper and analyzed as previously described in the other examples in this patent.

Example 10

Free-Radical Polymer Nano and Microencapsulation of AI's and Capsule Rupture

Internal Stress Enhancement Agents (ISEA) Systems

In this technology, an oil phase is made from a series of reactive vinyl or acrylic acid ester monomers and the AI. It is also possible to contain a water-insoluble solvent or oil along with the AI/reactive monomers in order to stabilize the oil phase. This oil is then dispersed into water along with surfactants or water-soluble polymers to create an emulsion. The degree of shear controls the size of the monomer droplets so that they can be made into nanometer, micrometer, or millimeter size ranges. Water-soluble or oil-soluble thermal initiators (peroxides) that are sensitive to heat or redox reactions are activated and the free radical polymerization takes place, which creates a wall around the AI or the solvents/oils/AI mixture and leads to the encapsulated AI product (U.S. Pat. No. 5,972,508).

Other micro or nanosize capsules of materials can be formed by creating a mixture of reactive acrylic monomers, initiators, and crosslinking monomers with a solvent or material to be encapsulated; combining this mixture with a combination of water and surfactants; and then sonicating the entire system to form a pre-emulsion that has nanosize droplets. The nanosize pre-emulsion is then heated to cause the free radical reaction to proceed and encapsulate the solvent or AI within the polymer shell. One can then take this first, encapsulated product and use it as the seed for a secondary acrylic polymerization process, so as to create a core/shell encapsulated product (WO/2009/146252). Additional references to free radical polymerization of acrylic esters can be found in Monomer/Acrylic Esters, E. H. Riddle, Book Division of Reinhold Publishing Co., New York, 1954. All of the prior art free radical polymerization techniques used to encapsulate AI's do not use or support or even suggest the types of polymer structural modification features or additions for enhanced controlled release of an AI that are embodied in this disclosure.

The first concern on a reactive monomer-to-polymer conversion process, whether it be free radical, cationic, reactive chemistry addition, or condensation, is that there must be no little chemical reaction occurring with the AI during the reactive encapsulation process.

Examples of a free radical polymerized encapsulation of a non-reactive AI (Pyriproxyfen) of this disclosure is shown in Table 29.

TABLE 29

| Free Radical Polymerization Encapsulation of Pyriproxyfen | | | | | | |
|---|---|---|---|---|---|---|
| Monomers (%) | $INDP_1$ | $IC_1$ | ISEA | $IC_2$ | Process | Results |
| MMA(80)<br>BA (10)<br>Styrene (10) | MMA<br>Styrene | — | — | — | Similar to U.S. Pat. No. 5,972,509 and WO/2009/146252 | No controlled release and the capsules were not attacked by water |
| MMA<br>BA<br>HEMA | MMA | HEMA | | | | No controlled release but the capsules were water sensitive |
| MMA<br>BA<br>HEMA<br>EGDMA | MMA | HEMA | EGDMA | | | No controlled release but the capsules swelled and cracked when soaked in water |
| MMA<br>BA<br>HEMA<br>EGDMA<br>Tween 20 | MMA | HEMA | EGDMA | Tween 20 | | Controlled release was effected |

Note:
Pyriproxyfen has a solubility of 1 × 106 mg/l in ethyl acetate, which is an excellent solvent for acrylic polymers; hence, the solvent parameters are similar to polymethyl methacrylate, which is a good INDP for the AI.
MMA is methylmethacrlate; BA is butylacrylate; HEMA is hydroxyl ethylmethacrylate; EGDMA is ethylene gylcol dimethacylate

Example 11

Natural Products and Modification of Natural Products for Controlled Release Systems There are a number of different natural products and modifications of natural products that have been made for different applications other than the controlled release of AI's, chemicals, or drug materials. For example, U.S. Pat. No. 7,645,818 shows the preparation of an ionic polymer system that contains a protein and carbohydrate-containing vegetable material component that serves as a reinforcement agent for a composite product. The vegetable seed component is selected from the group of soy spent flakes, defatted soy flour, or soy protein concentrates. The ionic polymers can be carboxylated poly(styrene-butadiene) or other acid functional polymer-like acrylics, polyurethanes, vinyls, and polyamides.

The concept described in WO/2004/12745 shows that hydrolyzed proteins can be modified to make personal care products. There a number of ways to modify the protein structures (U.S. Pat. Nos. 5,753,214; 4,474,694; 4,961,788; 4,687,826) and some forms of modified soy proteins are commercially available.

U.S. patent application 2009/0169867 uses soy flour or lignosulfonates in combination with emulsion polymers to make composites in a similar manner as U.S. Pat. No. 7,645,818.

Super absorbent polymer (SAP) materials based on free radical grafting of vinyl and acrylic or methacrylic acids and esters onto natural products (polysaccharides, chitin, cellulose starch, natural gums, xanthan, guar, alginates, proteins from soybean, fish, collagen-based proteins, and leaf-alfalfa) have been described in the Iranian Polymer Journal, Vol. 17 (6), 2008, pp 451-477.

There are also a number of references in the literature that disclose the modification of natural products to produce monomers that can be used to make polymers from these materials. Castor oil can be modified with acrylic acid to make a monomer with internal plasticization capabilities and soybean oils can be degraded into multifunctional alcohols to be reacted with isocyanates to make polyurethane foams. These polyols can also be esterified with acrylic acid to make multifunctional acrylates or epoxidized soybean structures can be reacted directly with acrylic acid to make new reactive monomer compounds.

Starch-based biodegradable polymers can also be made by blending in starch with a synthetic or natural base polymer, modification of the starch (physically or chemically), and graft copolymerization reactions of the starch for development of new products or incorporation into existing polymer structures (Express Polymer Letters, Vol. 3, No. 6, 2009, 366-375).

In this disclosure, we use modified natural products (NP) to form a basic AI-NP core structure for controlled release of the AI in a formulation. The modifications of the NP to form the core structure we use are as follows:

NP+AI

Hydrolysis of NP+AI

Blends of polymers and additives+AI

Free radical grafting of acrylic acid or acrylic monomer onto NP+AI\

Modification or functionalization of the NP+AI

Modification or functionalization (—OH, -00CCH═$CH_2$) of the NP+free radical or other monomer polymer grafting reactions+AI Soy and other vegetable-based acrylates to make polymers+AI Additional examples of national product modifications that are incorporated in this disclosure are described in Tables 30, 31, and 32.

TABLE 30

Polymers from Natural Products that Can Be Used in this Disclosure

| Formulation Ingredients (wt. gms) | Polymer Preparation Process | Polymer Properties |
|---|---|---|
| Vegetable oil [linseed, soya fatty ccid, soybean oil or tall oil] (58.5) trimellitic anhydride (20.2), phthalic anhydride (96.7), butyl carbitol (9.7), glycerol (12) | Cook to an acid number of 55, cool and neutralize with triethyl amine or Ammonium hydroxide [T. C. Patton, Alkyd Resin Technology, Interscience, Manual 8, 1962] | Water soluble or dispersible, depending on degree of neutralization |
| Soya fatty acid (290), rosin (100), phthalic anhydride (390), glycerol (220) | Cook to an acid number of 32, cool And neutralize with Triethyl amine [T. C. Patton, etc.] | Water soluble or dispersible, depending on degree of neutralization |
| Vegetable oil [dehydrogenated castor oil and soya fatty acid] (50/50), styrene, methylmethacrylate or methacrylic acid (8 to10% grafting modifications) | [F. Benner, et al., Official Digest, September 1959, 1143-1161 and T. C. Patton, etc. 158-160] | Solvent soluble, emulsifiable in water, depending on the acid level |
| 2-Ethylhexanoic acid (13.7), isophthalic acid (10.3), trimethyloethane (21), phenylethoxpolysiloxane (55) | [T. C. Patton, etc. 166-171 and B. H. Kress and H. A. Hopper, Official Digest, October 1952, 689-699 | Silicone-modified alkyd (solvent or water solutions or dispersions with surfactants) |
| Linseed fatty acid (57.7), toluene diisocyanate (25.1), glycerol (15.5) | [T. C. Patton, etc. 115-117] | Isocyanate, urethane-modified alkyds (solvent soluble or emulsified in water) |
| Commercial gums (xanthan, gum arabic, etc., polysaccharides) | Soluble/dispersible in water | Water-sensitive polymers |
| Phosphorus (P)-containing sugar or sorbitol polyols) | U.S. Pat. No. 3,694,430 | OH numbers of 284 and 5% P |
| Soybean acrylated monomers (16.95), ammonium, bicarbonate (0.42), rhodapex 10-436 (1.30) surfactant, water (112.24), butyl acrylate (16.50), ethylmethacrylate (12.65) and ammonium persulfate (0.82) | Standard polymerization procedures to make nano to miniemulsions depending on the agitation method [C. Quintero, et al., organic coatings, vol 57 (2006), 195-201] | AI can be in the polymerization process or post added in a solvent to the emulsion polymer particles through diffusion |

TABLE 30-continued

Polymers from Natural Products that Can Be Used in this Disclosure

| Formulation Ingredients (wt. gms) | Polymer Preparation Process | Polymer Properties |
|---|---|---|
| Soybean acrylated monomers can be made by reacting maleic anhydride with soybean oils followed by reaction with hydroxyethyl methacrylate | Standard polymerization procedures to make nano to miniemulsions depending on the agitation method [C. Quintero, et al., organic coatings, vol 57 (2006), 195-201] | These soybean acrylated monomers can be further reacted with acrylic/ methacrylic acids to make water soluble/dispersible polymers |
| Soy-based, thermo-sensitive hydrogels | U.S. Pat. No. 7,691,946 | — |

TABLE 31

| Biomaterials that Can Be Used in this Disclosure |
|---|
| Polymeric Biomaterials<br>Second edition<br>Editor, Severian Dunitriu<br>Marcel Dekker, Inc.<br>New York 2002 |
| Polyaspartic acids |
| Polyvinyl pyrrolidone/Vinyl acetate copolymers |
| Gantrez ® AN Copolymers (International Specialty Products) |
| poly(methyl vinyl ether/maleic anhydride and alcohol nanoesters |
| Hydrogels made by free radical polymerization of acrylamide monomers in the presence of Chitosan to form Semi-IPN and IPN Hydrogels (interpenetrating polymer materials) as described in Journal of Applied Polymer Science, Vol. 82, 2487-2496 (2001) and polymethanes of AI's (Journal of Applied Polymer Science, Vol. 82, 3109-3117 (2001) |
| Polysaccharide-grafted polymer particles (nm to 1 micron size ranges) as described in U.S. Pat. No. 7,144,852) |
| U.S. Pat. No. 4,087,298 describes polymers that are based on maleinized oils which are water dispersible or dilutable in water |
| Soy-based hydrogels U.S. Pat. No. 7,691,946 B2 |
| Polymers from triglyceride oils, Progress in polymer science, Vol. 31 (2006) pp 633-670 and references contained therin |
| Soy polyols with diisocyanates, J. appl. Polymer Science, vol. 77, 467-473 (2000) |
| Maleic anhydride modified soymeal, grafting of vinyl monomers to maleic anhydride modified soymeal and pretreatment of soymeal (partial hydrolysis) to produce intermediates and polymers for encapsulation (WO/2009/105753; $6^{th}$ annual meeting of the BIO/Environmrntally Degradable polymer society, abstracts, Sep. 17-20, 1997, San Diego, Calif.) |
| Synthesis of carboxy functional soybean acrylic-alkyd resins for water reducible coatings, JCT, Vol. 72,<br>No. 904, May 200, pp 55-61 |
| New hybrid latexes from soybean oils, Biomacromolecules, 2007, Vol. 8, No. 10, pp 3108-3114 |
| Acrylate modified natural fatty acids, US 2009/0156845 A1 |
| Starch based polymers, Polymer Letters, Vol. 3, No. 6, (2009) pp 366-375 |
| Combinations of soy flour and emulsion polymers for composites US 2009/0169867 A1 |
| Modified soy proteins in personal care products WO/2004/112745 and references cited therein |
| Ionic polymer composites comprising of proteins, carbohydrates and carboxylated polymers like acrylics and poly(styrene-butadiene), U.S. Pat. No. 7,645,818 B2 |
| Superabsorbant polymers as described in the Iranian Polymer Journal, Vol. 17, No(6), 2008, pp 451-477 |
| Biopolymer hydrogels, trends in food science and technology, 20(2009) pp 316-332 |
| Vinyl polymers grafted onto guar gum, Asian J. Exp. Sci., Vol. 19, No. 2, 2005, pp 77-81 |
| Miniemulsion polymerization of vegetable oil monomers, Progress in Organic Coatings, Vol. 57, issue 3, 1 Nov. 2006, pp 195-201 |
| Oils and emulsions described in Bailey's industrial oil and fat products, 6th edit., volumes 1-6, F. Shahidi editor, Wiley-Interscience, New York, 1945-2008 |
| Silicone alkyds, official digest, October 1952, pp 689-699 |
| Modification of alkyd resins with vinyl monomers, Official digest, September 1959, pp 1143-1161 |
| US 2009/0216040 A1 Polyols from oils using ozone |
| US 2004/0035517 Cellulosic fiber composites from protein hydrolysates |
| US 2010/0099802 A1 Protein stabilized latex polymer emulsions |

TABLE 32

| Soy and other Vegetable Oil Products that Can Be Used in this Disclosure |
|---|
| Hydrolysis products of soy protein materials (soy flour (Pargil) reacted with sodium carbonate or sodium hydroxide (WO/2005/100451) |
| Hydrolysis products of soy protein materials (soy flour (Pargil) reacted with sodium carbonate or sodium hydroxide (WO/2005/100451) but reacted with urea formaldehyde or grafted with acrylic/methacrylic acids |
| ARPRO ™1100, 3100 functional coating binders from ADM protein specialties |
| Soybond-40 from Weyerhaeuser |
| Pro-Coate ® 200 natural product extracted from soybeans |
| Vegetable oil derived polyols (US 2008/0262259A1; U.S. Pat. No. 6,624,244B2; Journal of Metals, Materials and Minerals, Vol. 17, No. 1, pp 17-23, 2007; Journal of Materials Science Letters, Vol. 19, pp 1355-1356, 200; Journal of Reinforced Plastics and Composites, Nov. 27, 2008, pp 1-8, EP1712576 AI;; US 2006/0041157A1; US 2007/0173626A9; US 2008/0262259AI; U.S. Pat. No. 6,759,542B2; and reference contained in the previous publications) |
| Polyurethane from Vegetable Oils, Polymer Review, 48: 109-155, 2008) |
| Malenized Oils, U.S. Pat. No. 4,097,298 |
| Malenized lubadiene and phenols (U.S. Pat. No. 4,322,470) the phenol could be replaced with lignin phenolic materials |
| Application of Vernonia Oil in Coatings, New Crop Proceedings, 1999, Vol. 4, 267-271 |
| Hybrid Latexes from a Soybean Oil-based Waterborne Polyurethane and Acrylic via Emulsion Polymerization, Yongshang Lu and Richard C. Larock, Bimacromolecules, 2007, Vol. 8 (10), pp 3708-3114 |
| Novel Synthesis of Carboxyl = functional Soybean Acrylic = alkyd Resins for Water = reducible Coatings, C. Wang, et. al, JCT, Vol. 72, No. 904, May, 2000, pp 55-61 |
| Natural fatty acid-based polymers (acrylate hybrid polymers (U.S. 2009/0156845AI) |
| Development of Polycon-complex Hydrogels, Trends and Food Science and Technology, 10 (2009), 316-332. |
| Polymers from Triglyceride Oils, Prog. Polym. Sci., Vol. 31, 2006, 633-670 and references contained herein |

Example 12

Natural Product Controlled Release Systems

There are a number of different natural products and modifications of natural products that can be made into controlled-release delivery systems for active ingredients. The following example discusses how natural products can be used within the embodiment of the disclosure.

Soy Meal and Soy Meal Hydrogels with 2,4,D-Amine Salt (AI)

High protein soy meal was supplied by Bunge, ADM, or Cargill (6 g was finely ground [<149 μm] and was combined with 14 g of acrylic acid, and 5 g of trimethylolpropane trimethacrylate in water [40% solids]). Ammonium persulfate initiator and sodium hydrogen sulfite reductant were added (0.15 g each) and the reaction was run with stirring at room temperature for 24 hours. The final product was a water-swollen hydrogel that was removed from the reaction vessel and dried (removal of the water) into a powder for use in an AI controlled-release experiment. Table 33 shows the results from a 2,4-D control (7.1 μl of a 23.5 g 2,4-D; 5.5 g isopropyl amine, 71 g DI water solution) applied to filter paper and dried. A 102.3 mg 2,4-D solution was applied to 40.6 mg soy meal and this mixture was applied to filter paper and dried. A mixture of dioctyl sulfosuccinates (AOT) surfactant and the 2,4-D on the soy meal (81 μg sample) was also applied to the filter paper and dried. A combination of the 2,4-D, soy meal mixture and a 50/50 by weight of Rovace/Rain Guard to make a 52 mg sample that was 93% soy meal, 4% 2,4-D, and 3% latex mixture applied to filter paper and dried. A combination of the 2,4-D, soy meal, latex, and AOT surfactant (66 mg sample that was 4.4% 2,4-D, 17.2% AOT; 1.86% latex blend and 76.54% soy meal) was also applied to filter paper and dried and the results for this series are shown in Table 33.

Table B shows the results for a 2,4-D control (7.1 μl of 23.5 g 2,4-D 4.4 isopropyl amine, 71 g DI water solution) and a mixture of 14.1 mg of the soy meal hydrogel with 27.4 mg 2,3-D amine salt solution to produce 1 to 3 mg samples that were 70% 2,4-D, and 30% soy meal and then applied to filter paper and dried.

Both Table 33 and Table 34 results show the advantage of the AI-soy meal (INP1) and AI-soy meal hydrogel (INDP1) and the different interface control ($IC_1$) materials (AOT, Latex, silicon oil) over that of the unprotected AI control alone.

TABLE 33

Soy Meal - 2.4-D Amine Salt Interaction Design Parameter ($INDP_1$) and Interface Control ($IC_1$) Studies

| Number of Washings and R Values | 2,4-D Amine Salt (Control) (% released) | 2,4-D Amine Salt + Soy Meal ($INDP_1$) (% released) | 2,4-D Amine Salt + Soy Meal + AOT ($IC_1$) (% released) | 2.4-D Amine Salt + Soy Meal + Latex (% released) | 2,4-D Amine Salt + Soy Meal + Latex ($IC_1$) + AOT ($IC_1$) (% released) |
|---|---|---|---|---|---|
| 1 | 94 | 36 | 37 | 35 | 23 |
| 2 | 6 | 17 | 15 | 13 | 14 |
| 33 | 0 | 15 | 8 | 13 | 14 |
| 4 | 0 | 7 | 8 | 10 | 14 |
| 5 | 0 | 6 | 8 | 5 | 9 |
| 6 | 0 | 6 | 6 | 5 | 7 |
| 7 | 0 | 4 | 6 | 5 | 7 |
| 8 | 0 | 3 | 6 | 5 | 4 |
| 9 | 0 | 3 | 3 | 5 | 4 |
| 10 | 0 | 2* | 3* | 4* | 4* |
| R | 2 | 10 | 10 | 10 | 10 |

*Not all of the sample was released after 10 washings.

TABLE 34

Soy Meal Hydrogel-2.4-D Amine Salt Interaction Design Parameter ($INDP_1$) and Interface Control ($IC_1$) Studies

| Number of Washings and R Values | 2,4-D Amine Salt Control (% released) | 2.4-D Amine Salt + Soy Meal Hydrogel ($INDP_1$) (% released) | 2.4-D Amine Salt + Soy Meal Hydrogel ($INDP_1$) + Silicon Oil ($IC_1$) (% released) |
|---|---|---|---|
| 1 | 94 | 24 | 10 |
| 2 | 6 | 19 | 10 |
| 3 | 0 | 14 | 10 |
| 4 | 0 | 7 | 10 |
| 5 | 0 | 7 | 8 |
| 6 | 0 | 7 | 8 |
| 7 | 0 | 7 | 10 |
| 8 | | 5 | 7 |
| 9 | 0 | 4 | 7 |
| 10 | 0 | 4* | 5* |
| R | 2 | 10 | 10 |

*Not all of the sample was released after 10 washings.

While the compositions and methods have been described with reference to various embodiments, those skilled in the art will understand that various changes may be made and equivalents may be substituted for elements thereof without departing from the scope and essence of the disclosure. In addition, many modifications may be made to adapt a particular situation or material to the teachings of the disclosure without departing from the essential scope thereof. Therefore, it is intended that the disclosure not be limited to the particular embodiments disclosed, but that the disclosure will include all embodiments falling within the scope of the appended claims. In this application all units are in the metric system and all amounts and percentages are by weight, unless otherwise expressly indicated. Also, all citations referred herein are expressly incorporated herein by reference.

Example 13

Insecticides

One of the major problems with insecticides is their inability to directly interact with and penetrate the shell of the insect, which is primarily a polymeric structure called chitin:

$(C_{16}H_{30}O_{10}N_2)$.

The McGinniss Equation parameters, $\chi_O$=0.39 and $\chi_N$=0.09 and a Log P=−0.3, indicate that this is a polar molecule and does not interact well with nonpolar insecticides (AI's) having low $\chi_O$ values and high $\chi_E$ and $\chi_{Cl}$ values as shown in Table 35.

TABLE 35

Properties of Selected Insecticides

| Insecticides | Water Solubility (mg/l) | Log P | $\chi_O$ | $\chi_N$ | $\chi_F$ | $\chi_{Cl}$ |
|---|---|---|---|---|---|---|
| Cyfluthrin | 0.0066 | 6 | 0.11 | 0.032 | 0.044 | 0.163 |
| Tefluthrin | 0.016 | 6.4 | 0.076 | — | 0.317 | 0.085 |

In order to design a system that allows the interaction of the nonpolar insecticides in Table 35 with the polar chitin substrate, one needs a surfactant that has a $\chi_O$ value lower than chitin and somewhat higher than the insecticides. Naphthalenesulfonate has a $\chi_O$ value of 0.23, as do some alkylphenol ethylene oxide substituted phenols, and a combination of these materials in a water dispersion of the AI's in Table 35 wetted the surface of the chitin causing a stain to be formed indicating a interaction had taken place. A pure water dispersion of the insecticides had no effect on wetting or absorbing onto the chitin surface.

Example 14

Leaf Penetration

In a study on the "Interaction of Surfactants and Leaf Surfaces in Glyphosate Absorption (Mority Knoche and M. J. Bukovac; Weed Science, Vol. 41, No. 1 (January-March, 1993), pp. 87-93, it was found that glyphosate alone has very little capability to penetrate leaf surfaces, such as, for example, sugar beet and kohlrabi plants. The sugar beet leaves have amorphous wax surfaces while the kohlrabi leaves have a fine crystalline wax on their surfaces. By combining the glyphosate with a series of polyethylene oxide substituted phenol surfactants, one observed that the leaf surfaces could be penetrated with these types of systems. The ethylene oxide (EO) substituted alkylphenols (EO units between 5 and 30) showed special situations where some structures increased the spreading or foliar uptake of the glyphosate while others decreased the ability of the glyphosate to absorb or interact with the leaf surfaces (Table 36)

TABLE 36

| Effect of Different Surfactant Structures on Glyphosate Interaction Capabilities with Waxy Leaf Surfaces | | | |
|---|---|---|---|
| Leaf | Glyphosate Absorption (%) | Decrease in Drop Area on Leaf ($mm^2$) | McGinniss Equation Parameter $\chi_o$ for Surfactants Used in This Study. |
| Sugar Beet | 12 | | 0.23 |
| Sugar Beet | 5 | | 0.32 |
| Sugar Beet | | 4 | 0.23 |
| Sugar Beet | | 3 | 0.32 |
| Kohlrabi | 17 | | o.23-0.30 |
| Kohlrabi | Less than 17 | | 0.32 |
| Kohlrabi | | 61 | 0.23 |
| Kohlrabi | | 2 | 0.32 |

Glyphosate has McGinniss Equation Parameters $\chi_O$=0.476; $\chi_N$=0.48 and $\chi_P$=0.18, which indicates that this is a very polar (high $\chi_O$ value) structure. It also has a high water solubility (10500 mg/l) and a Log P=−3.2. Because of its polar nature, it tends to stay or wash off a waxy leaf surface; thus, requiring a $INDP_n/IC_n$ material combination that is compatible with the glyphosate, while being able to wet or spread on the leaf surface and penetrate the wax barrier. Polyethylene oxide substituted phenols, where the number of ethylene oxide units varies between 5 and 30, have McGinniss Equation $\chi_O$ values between 0.23 (less polar) to 0.32 (more polar) and can be used to correlate the observations on glyphosate interacting with waxy leaf surfaces described in Table 36. The surfactants that showed the most promising interactions had $\chi_O$ values in the 0.23 to 0.30 range, which relates to surfactant structures that are relatively low to medium in polarity. Higher $\chi_O$ values (0.32 or greater) start to approach the $\chi_O$ values of glyphosate (0.476), which had no leaf penetration or interaction capability unless the right polarity surfactant was present in the formulation. This example illustrates the importance of understanding the properties of both the AI and the surfactant structures in order to design a efficient leaf-AI penetration system.

Example 15

Seed Treatments

Seed treatments are used to incorporate pesticides onto the seed coating and to decrease the disease susceptibility of the seed during its germination in the soil. The seed coating can alter the movement of water across the seed and the protective pesticide in the polymer of the seed coating can enhance both the germination and survival of the seed under adverse environmental conditions.

A good protective seed coating has a balance of water sensitive and non-water sensitive polymer materials. The McGinniss Equation $\chi_O$ (defined as the weight % of the oxygen atom(s) contained in the monomer repeat structure of the polymer) for polymers shown in Table 37 is a good indication of the water sensitivity of polymers ($INDP_n$) that can be used for seed coating applications. The higher the $\chi_O$ value the greater the water sensitivity of the polymer and the same is true for natural products or surfactants that can act as interface control ($IC_n$) agents to help in the controlled release of a pesticide or herbicide encased in the seed coating into the soil.

TABLE 37

| Water Sensitivities and $\chi_o$ (U.S. Pat. No. 4,566,906) | | |
|---|---|---|
| Polymers | Water Solubility in Polymer (Wt. %) | $\chi_o$ |
| Polystyrene | 0.048 | 0 |
| Polyvinyl isobutyl ether | 0.36 | 0.16 |
| Polyisobutyl methacrylate | 0.64 | 0.23 |
| Polyethyl methacrylate | 0.72 | 0.28 |
| Polymethyl methacrylate | 1.18 | 0.32 |
| Polyvinyl acetate | 2.2 | 0.37 |
| Polyhydroxyethyl methacrylate | 5-9 | 0.37 |
| Polymethacrylic acid | 10 | 0.37 |
| Polyhydroxyethyl acrylate | 10-18 | 0.41 |
| Polyacrylic acid | 18 | 0.44 |

It should also be noted that natural product, such as, for example, linseed oil, epoxidized soybean oil, shellac, furans and sucrose materials, have $\chi_O$ values of 0.11, 0.21, 0.32, 0.33, and 0.51, respectively, and can be used as $INDP_n/IC_n$ components for protective seed coatings and other applications as well.

A corn seed was coated with a control $INDP_1$ polymer (polyvinyl isobutyl ether) while another corn seed was coated with a 25/75 wt % blend of polyvinyl acetate ($IC_1$)/polyvinyl isobutyl ether and both placed in water for 2 days. The control polymer coated seed showed little to no signs of rupture while the polymer blend had become disbonded from the seed surface.

Example 16

Molecular Modeling of AI's Polymers and Other Materials

The electronic structure of any material (AI, polymer surfactant, etc.) is an important parameter that only can be obtained by molecular modeling on a computer. If one can obtain the electronic structure of an AI and map out its electronic charge density, then one has another parameter to use in the designing of a highly effective self assembly controlled release system.

Once one has the electronic structure of the AI mapped out, then one can computer model the charge densities of different types of polymers or surfactants to determine which structure has the greatest potential to interact strongly or weakly ($INDP_n$ or $IC_n$) with the AI and create the controlled release system.

The electronic charge density values for each AI atom 2,4-D (2,4-dichlorophenoxy acetic acid) is shown in Table 38. These electronic charge values were determined by computational modeling on a standard desktop computer using HyperChem™ Release 2 for windows Computer software program (Autodesk, Inc., Mar. 16, 1993; Scientific Modeling Division, 2320 Marinship Way, Sausalito, Calif. 94965).

The dipole moment for 2,4-D was calculated to be μ=2.03 and all the positive and negative values of the charges on each atom of the 2,4-D structure are tabulated in Table 38. From these charge density assignments, one can determine the most electronegative and electropositive regions of this molecule, which relates to where the strongest or weakest electronic attraction with other materials will take place. For example, the largest electronegative charge density is associated with the oxygen (1-O—) [−0.363] on carbon atom 1 (1C=Aromatic) and on the carboxyl functional group (COO) on O═ {double bond oxygen on carbon atom (8C═) [−0.189] and —O— the single oxygen atom on carbon atom (8C═) [−0.352]}.

Once one knows the areas and magnitude of highest and lowest electronegativity for the 2,4-D AI, one then can model different polymers to see if they have similar or different charge distributions and would this information help decide which polymer structure might be better for a self assembly controller release system with the 2,4-D molecule.

In Table 39 are the computer-generated models for the electron charge density distributions for all the atoms in the monomer repeat units for polyvinyl alcohol (PVOH) and polyacrylic acid (PAA). The calculated dipole moment for PVOH is μ=1.6 and the calculated dipole moment for PAA is μ=1.96; so, there is a very large difference between these two polymer structures and the dipole moment of PAA is very close to the dipole moment of the 2,4-D (μ=2.03).

The electronic structure for PVOH has the highest electronegative charge (−0.288) on the oxygen atom attached to carbon atom 1C.

The electronic structure for PAA has the most electronegative charge (−0.368) on the 30=(double bond oxygen atom attached to 3C) and 3-O— (single bond oxygen attached to 3C═O (−0.314, which is very similar to the electronegative charge distribution of 2,4-D.

2,4-D was added to both polymers and the 2,4-D-PAA (AI-INDP$_1$) combination showed a better controlled-release profile (slower release rate) than the 2,4-D-PVOH (AI-INDP$_2$) system. We believe that the PAA electronic structure had a strong interaction capability with 2,4-D, which influenced the controlled release properties of this system. These types of molecular modeling studies on AI-Polymer or other material potential interactions can be a new tool to help design new controlled release products.

TABLE 38

Molecular Modeling of 2,4-D (2,4-dichlorophenoxy acetic acid)

| Atoms ($C_8H_6Cl_2O_3$) Number Location Designation (1 through 8) | Electronic Charge Value Associated with Each Atom |
|---|---|
| 1C═ (Aromatic) | 0.124 |
| 2C═ (Aromatic) | 0.104 |
| 3C═ (Aromatic) | 0.010 |
| 4C═ (Aromatic) | 0.073 |
| 5C═ (Aromatic) | −0.009 |
| 6C═ (Aromatic) | 0.004 |
| 2Cl— (Chlorine Atom on Carbon Atom 2) | −0.113 |
| 4Cl— (Chlorine Atom on Carbon Atom 4) | 0.033 |
| 1-O— (Single Oxygen Atom on Carbon Atom 1) | −0.363 |
| 7C (Aliphatic) | 0.111 |
| H— (3C) (Hydrogen Atom on Carbon Atom 3) | 0.034 |
| H— (5C) (Hydrogen Atom on Carbon Atom 5) | 0.033 |
| H— (6C) (Hydrogen Atom on Carbon Atom 6( | 0.034 |
| H— (7C) (Hydrogen Atom on Carbon Atom 7) | 0.062 |
| H— (7C) (Hydrogen Atom on Carbon Atom 7) | 0.062 |
| 8C═ (O═C— on Carbon Atom 8 Attached to C7) | 0.283 |
| O═ (Double Bond Oxygen Atom on 8C═) (O═C) | −0.189 |
| —O— (Single Oxygen Atom on Carbon 8C═) (O═C—O—) | −0.352 |
| H— [Hydrogen Atom on Single Oxygen Atom on 8C═ [—O—(8C═)] (COOH) | 0.209 |

TABLE 39

Molecular Modeling of Monomer Repeat Units for Polyvinyl Alcohol (PVOH and Polyacrylic Acid (PAA)

| Monomer Repeat Unit Structure for Polymers | Electronic Charge Value Associated with Each Atom |
|---|---|
| PVOH Atoms $-(CH_2-CH)_n-$ with OH on CH; Number Location Designation (1 through 2) | |
| 1C (Aliphatic) | 0.011 |
| 2C (Aliphatic) | −0.182 |
| 1O (Single Oxygen Atom on Carbon Atom 1) | −0.288 |
| 1H (Hydrogen Atom on Oxygen Atom on Carbon Atom 1) | 0.171 |
| 1H— (Hydrogen Atom on Carbon Atom 1) | 0.047 |
| 2H— (Hydrogen Atom on Carbon Atom 2) | 0.061 |
| 2H— (Hydrogen Atom on Carbon Atom 2) | 0.067 |
| PAA Atoms $-(CH_2-CH)_n-$ with COOH on CH; Number Location Designation (1 through 3) | |
| 1C (Aliphatic) | −0.154 |
| 2C (Aliphatic) | −0.209 |
| 3C═ (Double Bond 3C Attached to Carbon atom 2) | 0.304 |
| 3O═ (Double Bond Oxygen Atom Attached to Double Bond 3C═) | −0.368 |
| 3-O— (Single Bond Oxygen Attached to 3C═O) | −0.314 |
| 3H— (Single Hydrogen Bond Attached to 3-O—) | 0.243 |
| 1H— (Hydrogen Atom on Carbon Atom 1) | 0.120 |
| 2H— (Hydrogen Atom on Carbon Atom 2) | 0.081 |
| 2H— (Hydrogen Atom on Carbon Atom 2) | 0.089 |

We claim:

1. A method for constructing a self-assembling polymeric particle bearing an active ingredient ("AI") and for treating soil or plant surfaces, which comprises the steps of:

(a) determining a solubility parameter for an AI;

(b) comparing the solubility parameter of the AI with a solubility parameter of a set of first polymers and selecting a first polymer having a Hansen solubility parameter, which is the total Hansen solubility parameter (δT) or any of δd, δh, δp, that is within at least 2 $MPa^{0.5}$ of a Hansen solubility parameter of the AI for forming an AI/first polymer stable blend, and forming the AI/first polymer stable blend;

(c) determining a second polymeric interface control agent having a Hansen solubility parameter that is at least 2 $MPa^{0.5}$ different than a Hansen solubility parameter of the first polymer in the AI/first polymer stable blend, and blending said second polymeric interface control agent with said AI/first polymer blend to form a second blend;

(d) making a water stable blend of said second blend; and (e) depositing said water stable blend upon a surface to form a self-assembled polymeric particle, said self-assembled polymeric particle having a core of said AI with said first polymer and said second polymeric interface control agent.

2. The method of claim 1, wherein the AI is combined with solubility parameter matched free radical or condensation type monomers, which monomers are polymerized in the presence of the AI to form nanometer or micrometer size AI encapsulated polymers.

3. The method of claim 1, wherein the AI is combined with polymer stabilizers and emulsified in water to form a nanometer or micrometer size emulsion that contains said AI.

4. The method of claim 1, wherein the solubility parameter matched first polymer is formed into nanometer or micrometer size particles and the AI is incorporated into said first polymer particles by contacting with an aqueous or non-aqueous dispersion of said AI or by vapor diffusing said AI into said first polymer particles.

5. The method of claim 1, wherein the solubility parameter matched first polymer is formed into a water/oil or oil/water emulsion of nanometer or micrometer sized particles of said solubility parameter matched first polymer and wherein the AI is diffused into the emulsion and becomes stabilized.

6. The method of claim 1, wherein said second blend is not stable in water and further comprising adding an additive to make the second blend stable in water.

7. The method of claim 1, wherein said self-assembling polymer particles are applied to one or more of soil, seed, or plant leaf.

8. The method of claim 1, wherein said AI is one or more of a fungicide, insecticide, or herbicide.

9. The method of claim 1, wherein said AI functions as a soil treatment, leaf treatment, seed treatment, or insect treatment.

10. The method of claim 1, wherein said AI is a natural product.

11. The method of claim 1, wherein said AI is one or more of a solid, liquid, solids dispersion in water, solids dispersion in an organic solvent, solids dispersion in a vegetable oil, homogeneous solution in water, homogeneous solution in an organic solvent, or homogeneous solution in a vegetable oil.

* * * * *